US010301675B2

(12) United States Patent
Gong et al.

(10) Patent No.: US 10,301,675 B2
(45) Date of Patent: May 28, 2019

(54) COMPOSITIONS AND METHODS FOR REDUCING INHIBITION OF RT-PCR

(71) Applicant: Bio-Rad Laboratories, Inc., Hercules, CA (US)

(72) Inventors: Xiao-Song Gong, Berkeley, CA (US); Yan Wang, San Francisco, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 242 days.

(21) Appl. No.: 14/926,461

(22) Filed: Oct. 29, 2015

(65) Prior Publication Data

US 2016/0046982 A1 Feb. 18, 2016

Related U.S. Application Data

(63) Continuation of application No. 13/681,326, filed on Nov. 19, 2012, now Pat. No. 9,200,318, which is a continuation of application No. 12/323,256, filed on Nov. 25, 2008, now Pat. No. 8,338,094.

(60) Provisional application No. 61/004,516, filed on Nov. 27, 2007.

(51) Int. Cl.
*C12Q 1/686* (2018.01)
*C12Q 1/6844* (2018.01)
*C07K 14/195* (2006.01)

(52) U.S. Cl.
CPC ............ *C12Q 1/686* (2013.01); *C07K 14/195* (2013.01); *C12Q 1/6844* (2013.01)

(58) Field of Classification Search
CPC ............ C12Q 1/6844; C12Q 2527/125; C12Q 2527/127; C12Q 1/686; C12Q 2521/307
See application file for complete search history.

(56) References Cited

U.S. PATENT DOCUMENTS

| | | | |
|---|---|---|---|
| 5,264,423 A | 11/1993 | Cohen et al. | |
| 5,407,800 A * | 4/1995 | Gelfand | C12N 9/1252 435/6.11 |
| 5,935,834 A | 8/1999 | Odawara | |
| 6,300,069 B1 | 10/2001 | Missel et al. | |
| 6,495,350 B1 | 12/2002 | Lee et al. | |
| 6,667,165 B2 | 12/2003 | Peters | |
| 6,830,902 B1 | 12/2004 | Astatke et al. | |
| 7,122,316 B2 | 10/2006 | Adams et al. | |
| 2003/0082581 A1 | 5/2003 | Legerski | |
| 2003/0113712 A1 | 6/2003 | Lee et al. | |
| 2004/0002076 A1 | 1/2004 | Wang et al. | |
| 2004/0259115 A1 | 12/2004 | Schuster et al. | |
| 2006/0275792 A1 | 12/2006 | Lee et al. | |

FOREIGN PATENT DOCUMENTS

| | | |
|---|---|---|
| WO | 90/012022 A1 | 10/1990 |
| WO | 01/092501 A1 | 12/2001 |

OTHER PUBLICATIONS

Ciafre, S.A. et al., Nucl. Acids Res., vol. 23, pp. 4134-4142 (1995).*
Boulme, F. et al., Modified (PNA, 2'-O-methyl and phosphoramidite) anti-TAR antisense oligonucleotides as strong and specific inhibitors of in vitro HIV-1 reverse transcription, Nucl. Acids Res., vol. 26, pp. 5492-5500 (Year: 1998).*
Boiziau, et al., "A phosphorothioate oligonucleotide blocks reverse transcription via an antisense mechanism" FEBS Letters, 1994, vol. 340, pp. 236-240.
Chandler et al. "Reverse Transcriptase (RT Inhibition of PCR at Low Concentrations of Template and Its Implications for Quantitative RT-PCR," Applied and Environmental Microbiology, 1998, vol. 64, No. 2, pp. 669-677.
Choli, Theodora et al. "Isolation, characterization and microsequence analysis of a small basic methylated DNA-binding protein from the Archaebacterium, *Sulfolobus solfataricus*," Biochimica et Biophysica Acta, vol. 950, pp. 193-203 (1988).
Edmondson et al. "DNA-Binding Proteins Sac7d and Ss07d from Sulfolobus," Methods in Enzymology, 2001, vol. 334, pp. 129-145.
Goodman, N.C. et al. "Distinguishing reverse transcriptase of an RNA tumor virus from other known DNA polymerases," PNAS USA, vol. 68, pp. 2203-2206 (1971).
Liss, "Improved quantitative real-time RT-PCR for expression profiling of individual cells," Nucleic Acids Research, 2002, vol. 30, No. 17, 9 pages.
Majumdar, et al., "PCR inhibition by reverse transcriptase Reverse Transcriptase: Primer function of phosphorothioate oligodeoxynucleotide", Biochecmistry, 1989, vol. 28, pp. 1340-1346.Biochemistry, vol. 28, pp. 1340-1346 (1989).
Marshall, W.S. et al. "Inhibition of human immunodeficiency virus activity by phosphorodithioate oligodeoxycytidine," PNAS USA, vol. 89, pp. 6265-6269 (1992).
Ono, K. et al. "Differential inhibition of various deoxyribonucleic and ribonucleic acid polymerases by suramin," Eur. J. Biochem., vol. 172, pp. 349-353 (1988).
Promega PCR Master Mix, Part# 9PIM750, Promega Corporation, 2 pages (Revised Mar. 2007).
Sellner et al. "Reverse transcriptase inhibits Taq polymerase activity," Nucleic Acids Research, 1992, vol. 20, No. 7, pp. 1487-1490.
Stratagene Catalog, Gene Characterization Kits, p. 39 (1988).
SuperScript™ One-Step RT-PCR with Platinum® Taq, Invitrogen Life Technologies, Catalog No. 10928 (Jul. 2003).
Suslov et al. "PCR inhibition by reverse transcriptase leads to an overestimation of amplification efficiency," Nucleic Acids Research, 2005, vol. 33, No. 20, pp. 1-12.
Tabor, S., Curr. prot. Mol. Biol., 3.7.1-3.7.3 (1987).
Wang et al. "A novel strategy to engineer DNA polymerases for enhanced processivity and improved performance in vitro," Nucleic Acids Research, 2004, vol. 32, No. 3, pp. 1197-1207.

(Continued)

*Primary Examiner* — Teresa E Strzelecka
(74) *Attorney, Agent, or Firm* — Kilpatrick Townsend and Stockton LLP

(57) ABSTRACT

In one aspect, compositions and methods for reducing reverse transcriptase (RT) inhibition in RT-PCR are provided. In some embodiments, the RT inhibition reducer is a phosphorothioate oligodeoxycytosine (SdC), phosphorothioate oligodeoxyadenine (SdA), phosphorothioate oligodeoxythymine (SdT), or phosphorothioate oligodeoxyguanosine (SdG).

12 Claims, 28 Drawing Sheets

(56) References Cited

OTHER PUBLICATIONS

Dirani-Diab, et al., "Phosphorothioate oligonucleotides derived from human immunodeficiency virus type 1 (HIV-1) primer trnalys3 are strong inhibitors of HIV-1 reverse transcriptase and arrest viral replication in infected cells, antimicrobial agents and chemotherapy", American Sociecty for Microbiology, vol. 41, No. 10, Oct. 1997, pp. 2141-2148.

Marshall, et al., "Inhibition of human immunodeficiency virus activity by phosphorodithioate oligodeoxycytidine.", Proceedings of the National Academy of Sciences, vol. 89, No. 14, Jul. 15, 1992, pp. 6265-6269.

Matsukura, et al. "Phosphorothioate analogs of oxigodeoxynucleotides: Inhibitors of replication and sytopathic effects of human immunodeficiency virus", Proc. Natl. Acad. Sci. USA, 1987, vol. 84, pp. 7706-7710.

* cited by examiner

COMPOSITIONS AND METHODS FOR REDUCING INHIBITION OF RT-PCR

CROSS-REFERENCES TO RELATED APPLICATIONS

This application is a continuation of U.S. application Ser. No. 13/681,326, filed Nov. 19, 2012, which is a continuation of U.S. application Ser. No. 12/323,256, filed Nov. 25, 2008, now U.S. Pat. No. 8,338,094, which claims priority to U.S. Provisional Application No. 61/004,516, filed Nov. 27, 2007, each of which is incorporated in its entirety herein.

BACKGROUND OF THE INVENTION

The detection, analysis, transcription, and amplification of nucleic acids are the most important procedures in modern molecular biology. The application of such procedures for RNA analysis is especially important in the investigation of gene expression, diagnosis of infectious agents or genetic diseases, the generation of cDNA, and analysis of retroviruses, to name but a few applications. The reverse transcription of RNA, followed by polymerase chain reaction amplification, commonly referred to as RT-PCR, has become widely used for the detection and quantification of RNA.

The RT-PCR procedure involves two separate molecular syntheses: (i) the synthesis of cDNA from an RNA template; and (ii) the replication of the newly synthesized cDNA through PCR amplification. RT-PCR can be performed under three general protocols: (1) uncoupled RT-PCR, also referred to as two-step RT-PCR; (2) single enzyme coupled RT-PCR (coupled RT-PCR is also referred to as one-step RT-PCR or continuous RT-PCR), in which a single polymerase is used for both the cDNA generation from RNA as well as subsequent DNA amplification; and (3) two (or more) enzyme coupled RT-PCR, in which at least two separate polymerases are used for initial cDNA synthesis and subsequent replication and amplification.

In uncoupled RT-PCR, reverse transcription is performed as an independent step using buffer and reaction conditions optimal for reverse transcriptase activity. Following cDNA synthesis, an aliquot of the RT reaction product is used as template for PCR amplification with a thermostable DNA Polymerase, such as Taq DNA Polymerase, under conditions optimal for PCR amplification.

In coupled RT-PCR, reverse transcription and PCR amplification are combined into a single reaction mixture. Single enzyme RT-PCR utilizes the reverse transcriptase activity of some DNA polymerases, such as Taq DNA Polymerase and Tth DNA polymerase, whereas two-enzyme RT-PCR typically uses a retroviral or bacterial reverse transcriptase (e.g., AMV-RT, MMLV-RT, HIV-RT, EIAV-RT, RAV2-RT, *Carboxydothermus hydrogenoformans* DNA Polymerase or a mutant, variant or derivative thereof), and a thermostable DNA polymerase (e.g., Taq, Tbr, Tth, Tih, Tfi, Tfl, Pfu, Pwo, Kod, VENT, DEEPVENT, Tma, Tne, Bst, Pho, Sac, Sso, ES4 and others or a mutant, variant or derivative thereof).

Coupled RT-PCR provides numerous advantages over uncoupled RT-PCR. Coupled RT-PCR requires less handling of the reaction mixture reagents and nucleic acid products than uncoupled RT-PCR (e.g., opening of the reaction tube for component or enzyme addition in between the two reaction steps), and is therefore less labor intensive, reducing the required number of person hours. Coupled RT-PCR also requires less sample, and reduces the risk of contamination (Sellner and Turbett, 1998).

Single enzyme coupled RT-PCR, is the simplest RT-PCR procedure to date. This system is expensive to perform, however, due to the amount of DNA polymerase required. In addition, the single enzyme coupled RT-PCR method has been found to be less sensitive than uncoupled RT-PCR (Cusi et al., 1994), and limited to polymerizing nucleic acids of less than one kilobase pair (>1 kb) in length. Two enzyme RT-PCR systems show increased sensitivity over the single enzyme system generally, even when coupled in a single reaction mixture. This effect has been attributed to the higher efficiency of reverse transcriptase in comparison to the reverse transcriptase activity of DNA polymerases (Sellner and Turbett, 1998).

Although the two enzyme coupled RT-PCR system is more sensitive than the uncoupled protocol, reverse transcriptase has been found to interfere with DNA polymerase during the replication of the cDNA, thus reducing the sensitivity and efficiency of this technique (Sellner et al., 1992; Aatsinki et al., 1994; Mallet et al., (1995)). A variety of solutions to overcome the inhibitory activity of reverse transcriptase on DNA polymerase have been tried, including: increasing the amount of template RNA, increasing the ratio of DNA polymerase to reverse transcriptase, adding modifier reagents that can reduce the inhibitory effect of reverse transcriptase on DNA polymerase (e.g., non-homologous tRNA, T4 gene 32 protein, sulfur or acetate-containing molecules,), and heat-inactivation of the reverse transcriptase before the addition of DNA polymerase.

All of these modified RT-PCR methods have significant drawbacks, however. Increasing the amount of template RNA is not possible in cases where only limited amounts of sample are available. Individual optimization of the ratio of reverse transcriptase to DNA polymerase is not practicable for ready-to-use reagent kits for one-step RT-PCR. The net effect of currently proposed modifier reagents to relieve reverse transcriptase inhibition of DNA polymerization is controversial and in dispute: positive effects due to these reagents are highly dependent on RNA template amounts, RNA composition, or can require specific reverse transcriptase-DNA polymerase combinations (see, for example, Chandler et al., 1998). Finally, heat inactivation of the reverse transcriptase before the addition of the DNA polymerase negates the advantages of the coupled RT-PCR and carries with it all the disadvantages of uncoupled RT-PCR systems discussed earlier.

Because of the importance of RT-PCR applications, a one-step RT-PCR system with reduced RT inhibition, in the form of a generalized ready-to-use composition, which exhibits high sensitivity, requires a small amount of initial sample, reduces the amount of practitioner manipulation, minimizes the risks of contamination, minimizes the expense of reagents, is not restricted to the use of specific reaction buffers, and maximizes the amount of nucleic acid end product is needed in the art.

SUMMARY OF THE INVENTION

It has been discovered that reverse transcriptase (RT) inhibition in RT-PCR can be reduced by performing RT-PCR in the presence of suramin, Sso7d, a phosphoro oligodeoxynucleotide, AluI methylase or poly(rA)(dT)$_n$, or any combination thereof.

RT-PCR is one molecular manipulation used to generate and replicate a nucleic acid derived from an RNA template. RT-PCR is described herein as an exemplary protocol capable of utilizing the compositions and methods of the present invention. It will be readily understood by one of ordinary skill in the art that the present invention has utility in other processes, which involve a combination of reverse transcriptase and DNA polymerase activity. RT-PCR involves two separate molecular syntheses: (i) the synthesis of cDNA from an RNA template; and (ii) the replication of the newly synthesized cDNA through PCR amplification.

In one embodiment, the present invention provides a method for amplifying a nucleic acid molecule, including mixing an RNA template with a composition having a reverse transcriptase, a DNA polymerase and a RT inhibition reducer that can be Sso7d, Sac7d, Sac7e, Sso7e, AluI methylase, suramin, a phosphorothioate oligodeoxycytosine, a phosphorothioate oligodeoxyadenine, a phosphorothioate oligodeoxythymine or poly(rA)(dT). The method also includes incubating the mixture under conditions sufficient to synthesize a DNA molecule complementary to all or a portion of the RNA template, thereby amplifying the nucleic acid molecule.

In a second embodiment, the present invention provides a composition including a reverse transcriptase, a DNA polymerase, and a RT inhibition reducer that can be Sso7d, Sac7d, Sac7e, Sso7e, AluI methylase, suramin, a phosphorothioate oligodeoxycytosine (SdC), a phosphorothioate oligodeoxyadenine, a phosphorothioate oligodeoxythymine or poly(rA)(dT).

In a third embodiment, the present invention provides a kit including a first solution mixture including a DNA polymerase and a RT inhibition reducer that can be Sso7d, Sac7d, Sac7e, Sso7e, AluI methylase, suramin, a phosphorothioate oligodeoxycytosine (SdC), a phosphorothioate oligodeoxyadenine, a phosphorothioate oligodeoxythymine or poly(rA)(dT). The kit optionally includes at least one of buffers, nucleotides, salts, stabilizers, instructions, primers, RNA templates, dyes and nuclease-free water.

BRIEF DESCRIPTION OF THE DRAWINGS

FIG. 1a shows the log starting quantity in nanograms versus threshold cycle in the absence of SSO7d. FIG. 1b shows temperature versus −d(FRU)/dT in the absence of SSO7d. FIG. 1c shows the log starting quantity in nanograms versus threshold cycle in the presence of 0.1 µM SSO7d. FIG. 1d shows temperature versus −d(FRU)/dT in the presence of 0.1 µM SSO7d. FIG. 1e shows the log starting quantity in nanograms versus threshold cycle in the presence of 0.2 µM SSO7d. FIG. 1f shows temperature versus −d(FRU)/dT in the presence of 0.2 µM SSO7d.

FIG. 2a shows the log starting quantity in nanograms versus threshold cycle in the presence of 2.5 µM AluI Methylase. FIG. 2b shows temperature versus −d(FRU)/dT in the presence of 2.5 µM AluI Methylase. FIG. 2c shows the log starting quantity in nanograms versus threshold cycle in the absence of AluI Methylase. FIG. 2d shows temperature versus −d(FRU)/dT in the absence of AluI Methylase.

FIG. 3a shows cycle versus RFU in the absence of suramin. FIG. 3b shows the log starting quantity in nanograms versus threshold cycle in the absence of suramin. FIG. 3c shows temperature versus −d(FRU)/dT in the absence of suramin. FIG. 3d shows the log starting quantity in nanograms versus threshold cycle in the presence of 4 ng/µl suramin. FIG. 3e shows cycle versus RFU in the presence of 4 ng/µl suramin. FIG. 3f shows temperature versus −d(FRU)/dT in the presence of 4 ng/µl suramin.

FIG. 4a shows the log starting quantity in nanograms versus threshold cycle in the presence of 0.1 nM SdC. FIG. 4b shows temperature versus −d(FRU)/dT in the presence of 0.1 nM SdC. FIG. 4c shows the log starting quantity in nanograms versus threshold cycle in the presence of 0.5 nM SdC. FIG. 4d shows temperature versus −d(FRU)/dT in the presence of 0.5 nM SdC. FIG. 4e shows the log starting quantity in nanograms versus threshold cycle in the presence of 2 nM SdC. FIG. 4f shows temperature versus −d(FRU)/dT in the presence of 2 nM SdC. FIG. 4g shows the log starting quantity in nanograms versus threshold cycle in the presence of 10 nM SdC. FIG. 4h shows temperature versus −d(FRU)/dT in the presence of 10 nM SdC.

FIG. 5a shows the log starting quantity in nanograms versus threshold cycle in the presence of 10 ng Poly(rA)/dT. FIG. 5b shows temperature versus −d(FRU)/dT in the presence of 10 ng Poly(rA)/dT. FIG. 5c shows the log starting quantity in nanograms versus threshold cycle in the absence of Poly(rA)/dT. FIG. 5d shows temperature versus −d(FRU)/dT in the absence of Poly(rA)/dT.

DETAILED DESCRIPTION OF THE INVENTION

Figure 1A:
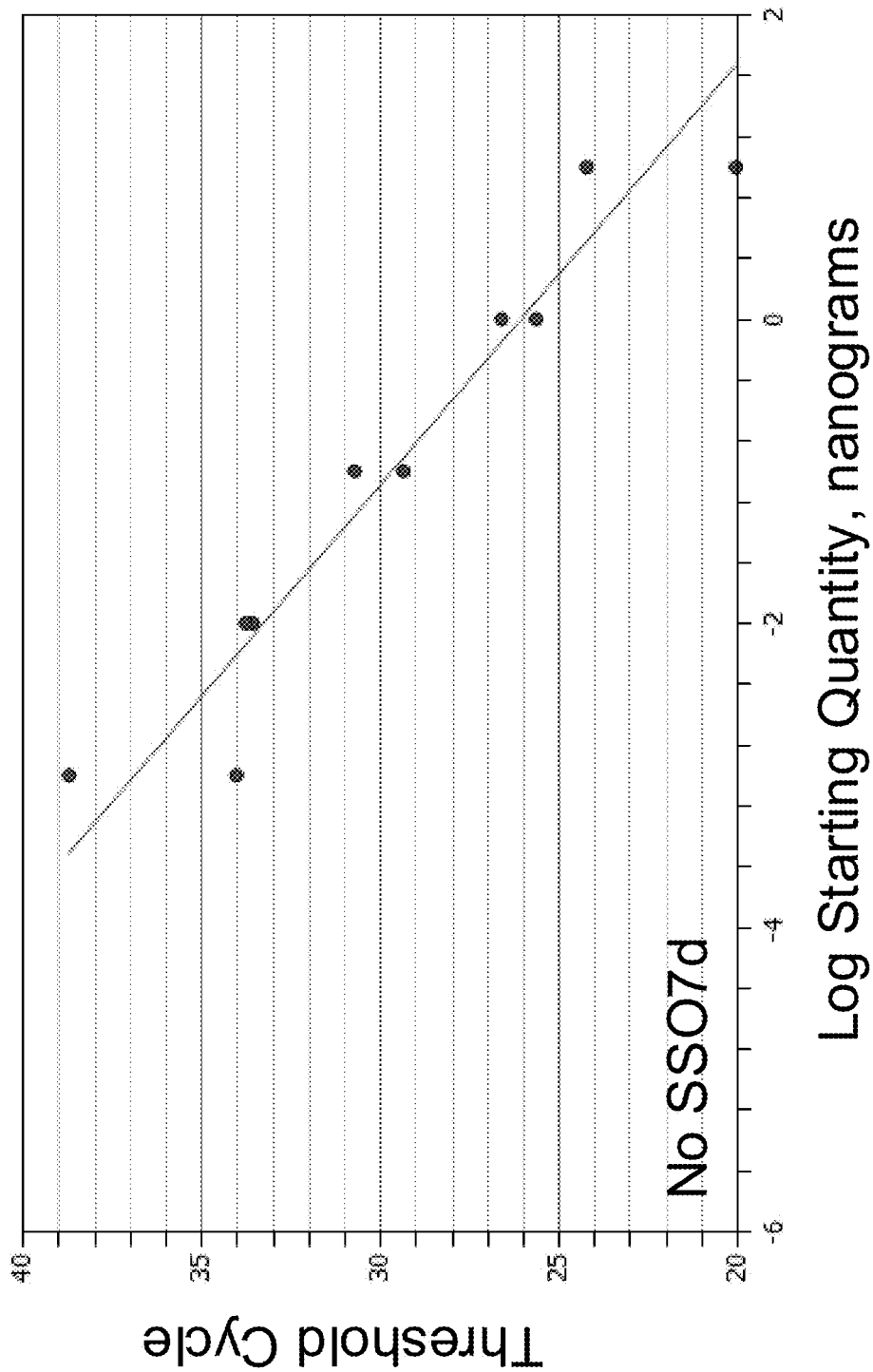
FIGS. 1a-1f show that addition of sequence non-specific double-stranded DNA binding protein SSO7d reduces the inhibition of reverse transcriptase and improves the specificity of one-step RT-PCR.
Figure 1B:
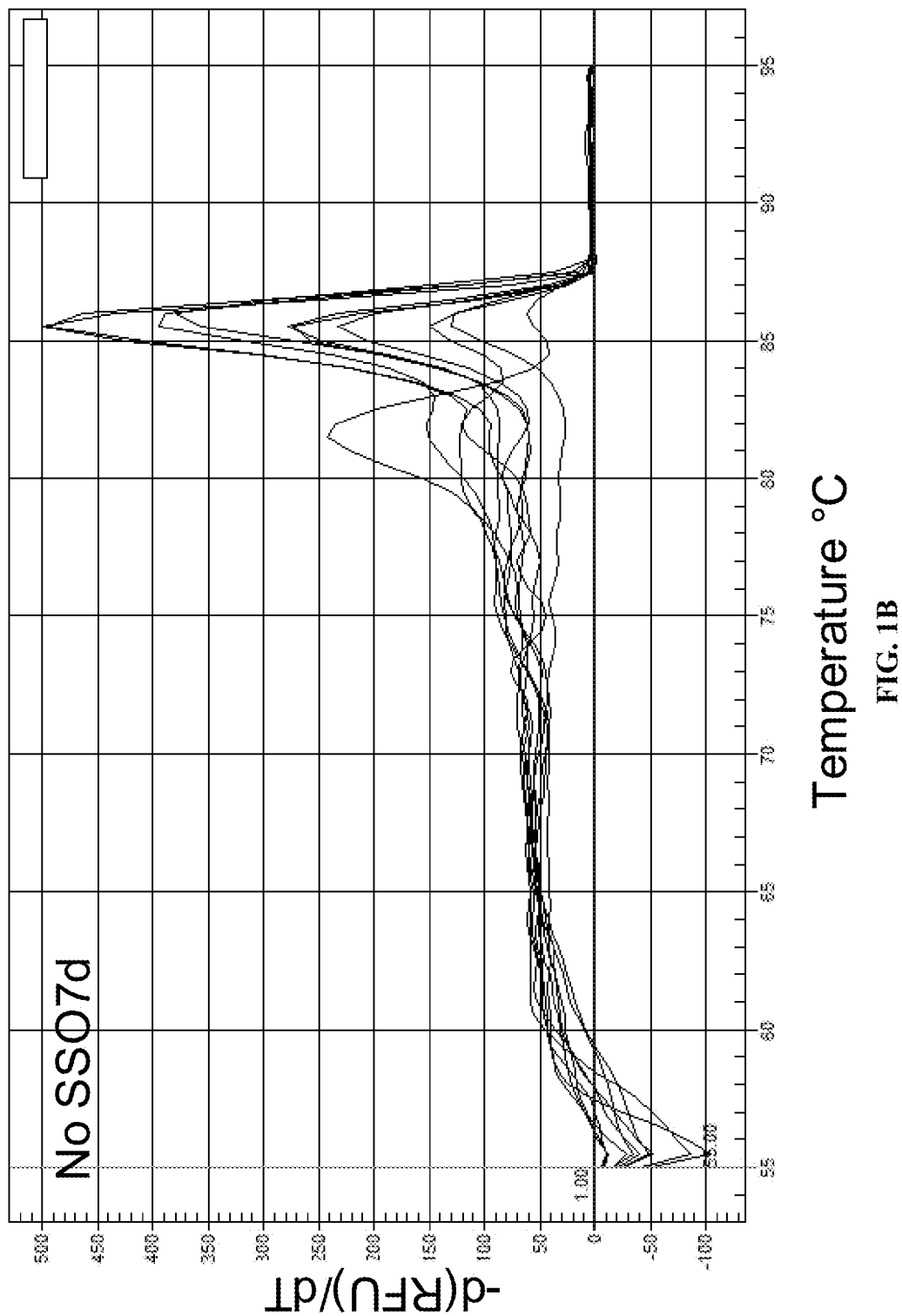
Figure 1C:
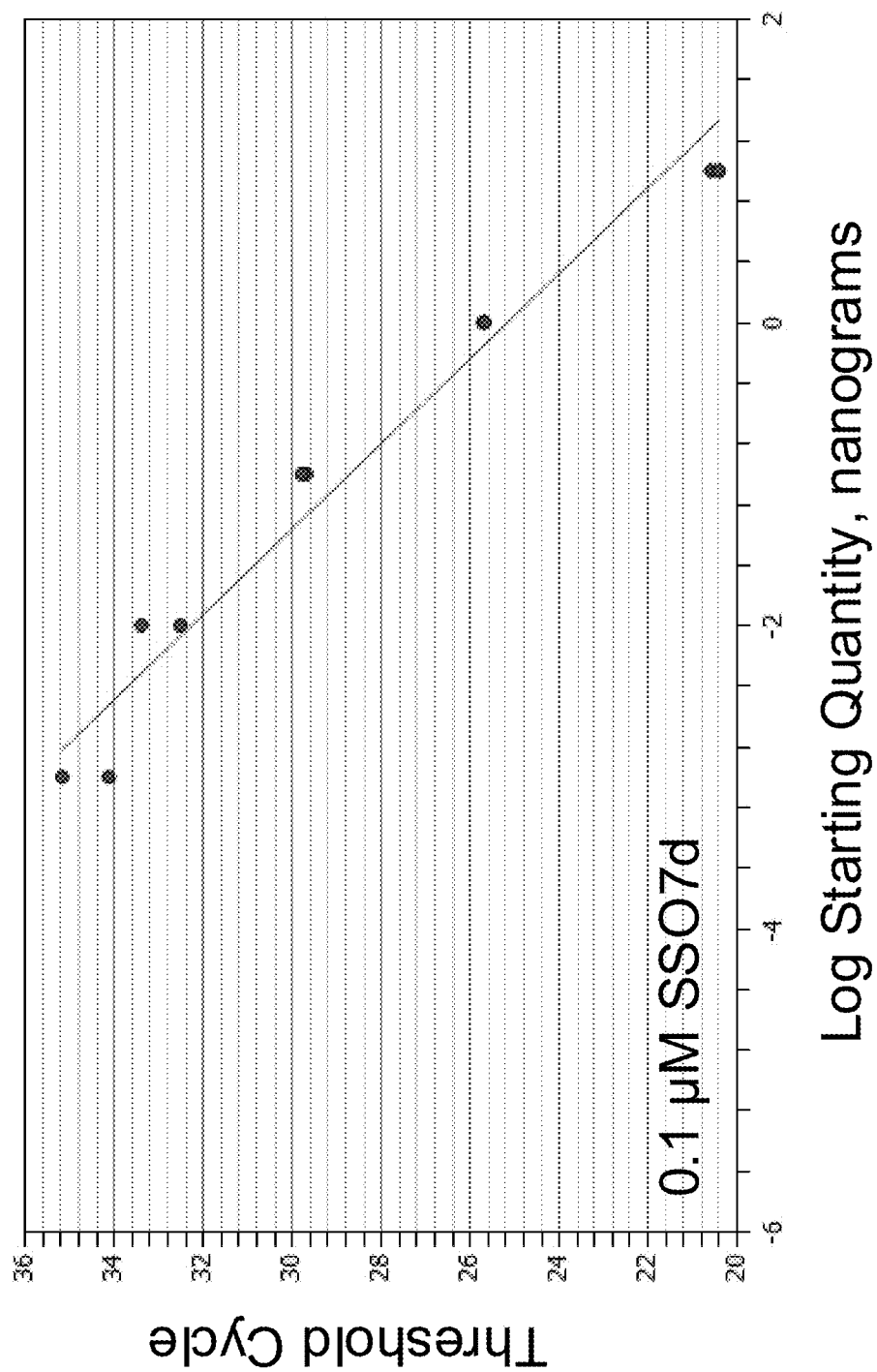
Figure 1D:
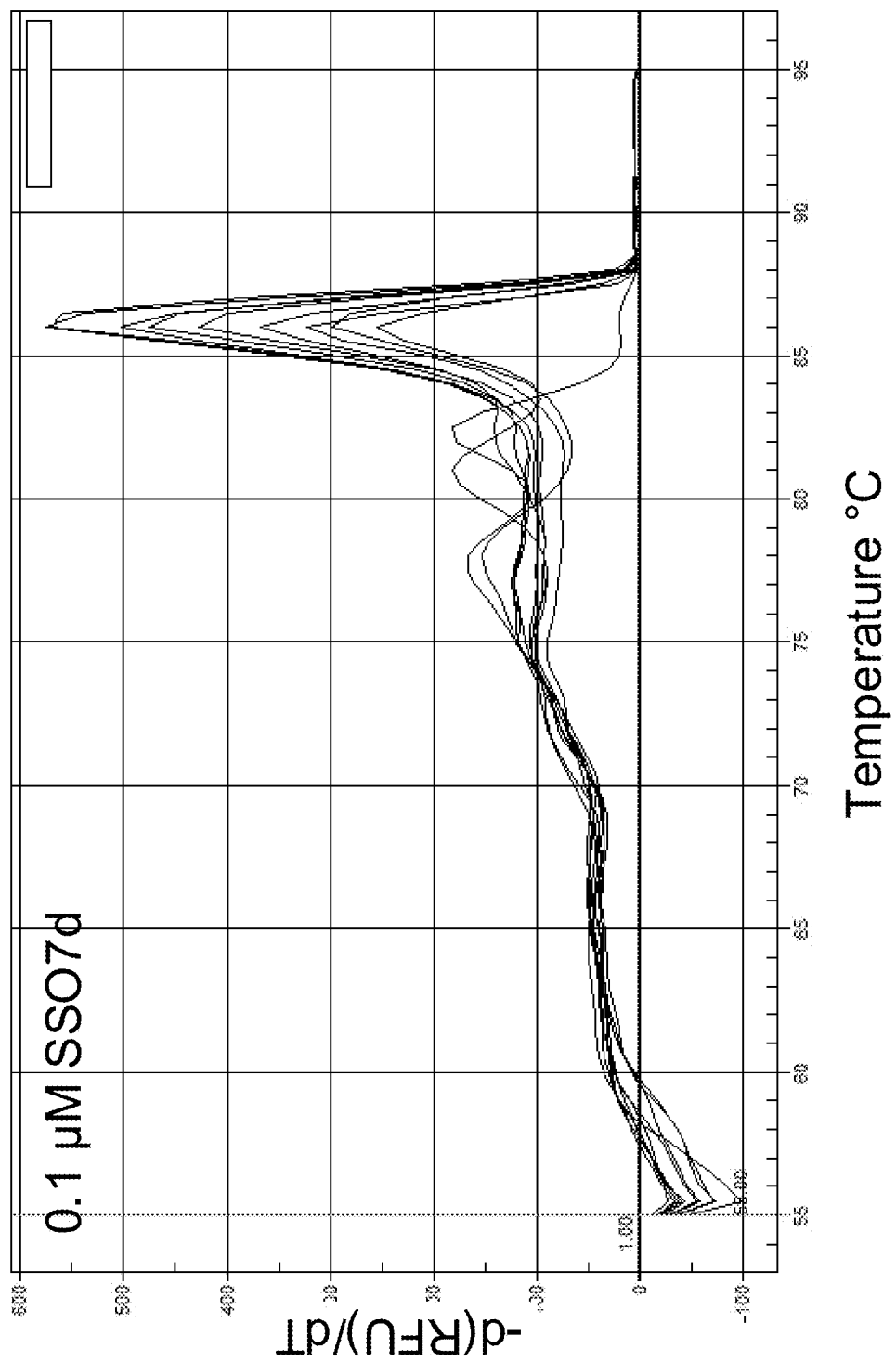
Figure 1E:
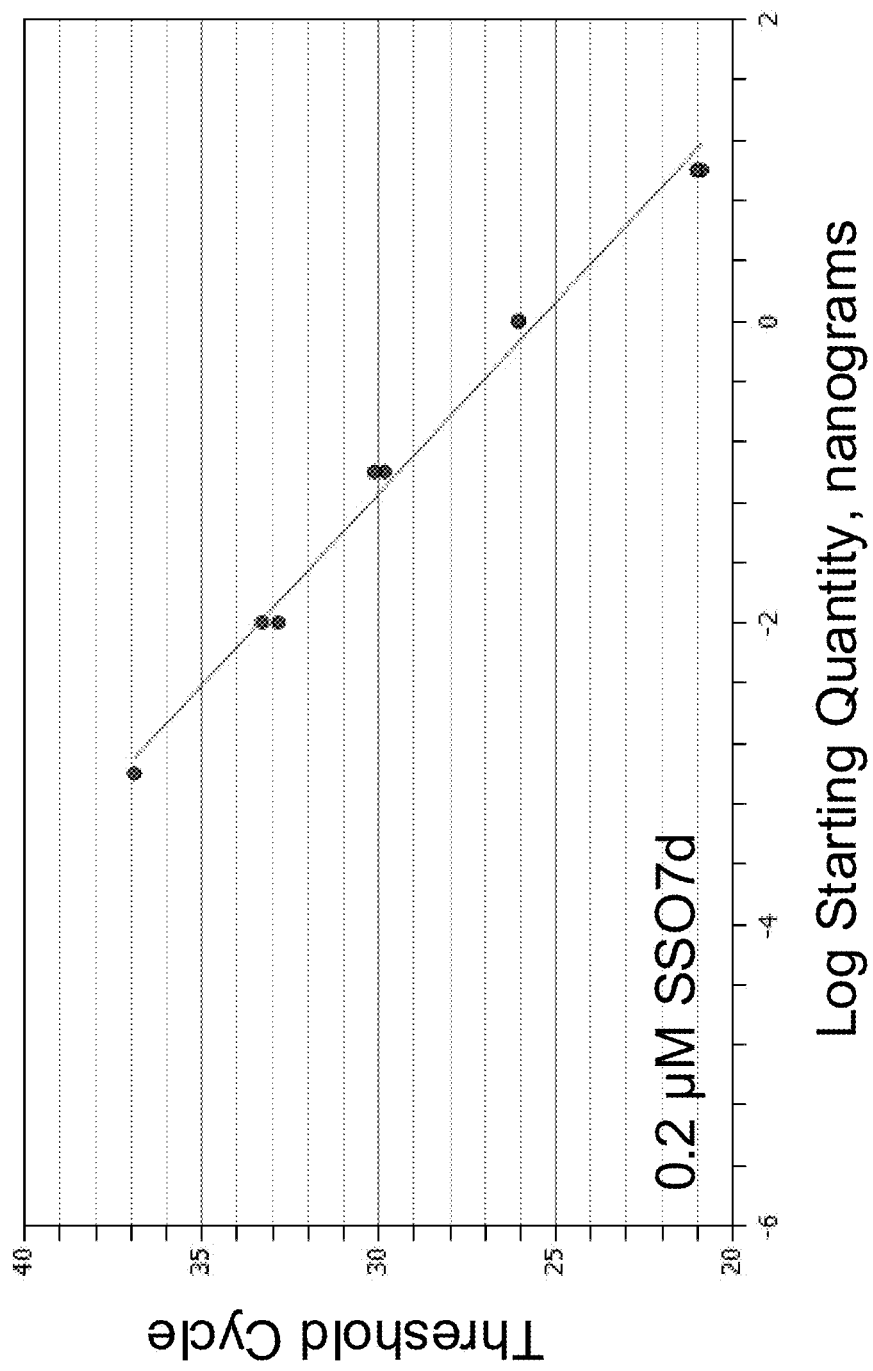
Figure 1F:
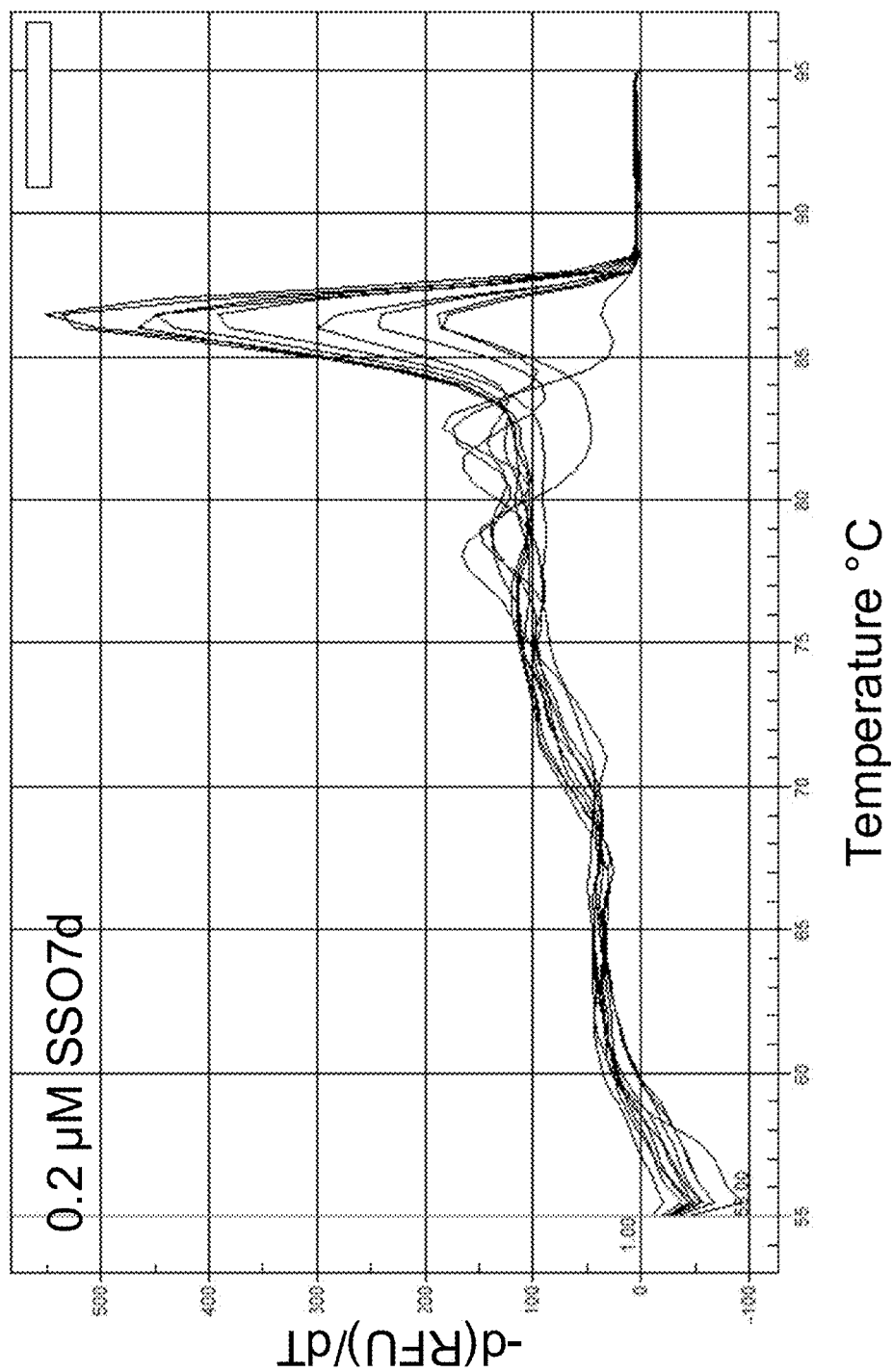
Figure 2A:
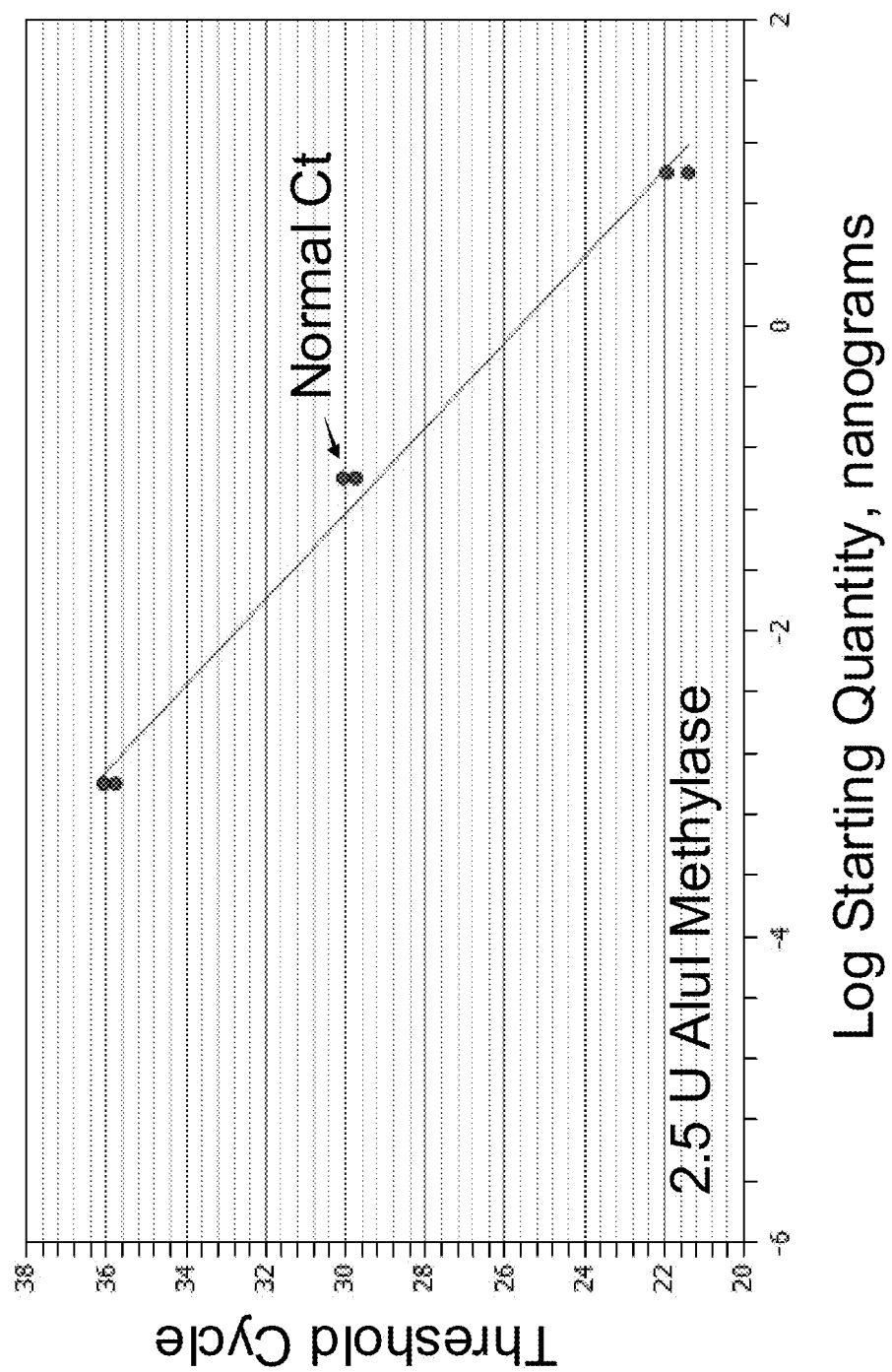
FIGS. 2a-2d show that addition of Alu methylase reduces the inhibition of reverse transcriptase and improves the specificity of one-step RT-PCR.
Figure 2B:
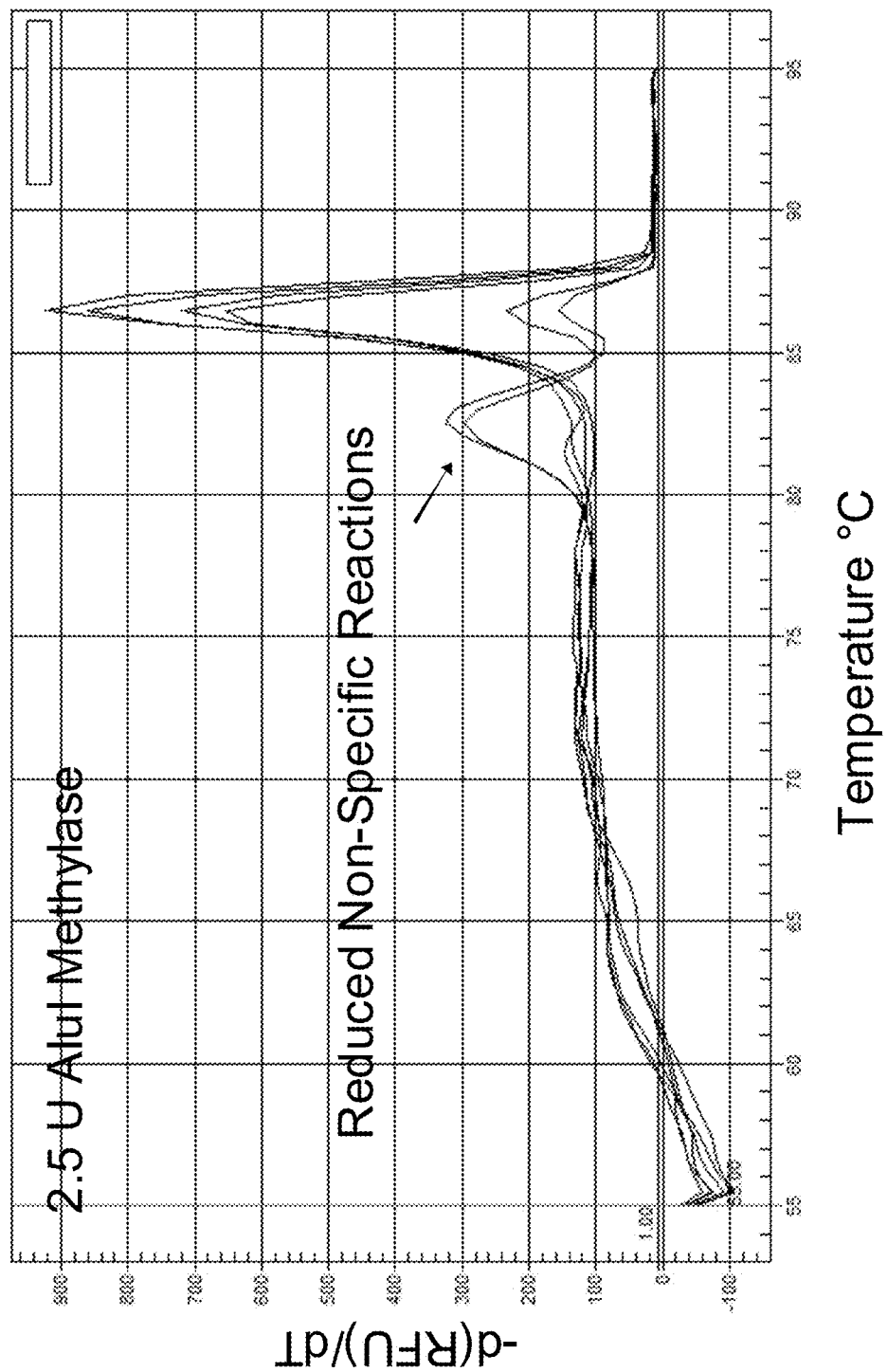
Figure 2C:
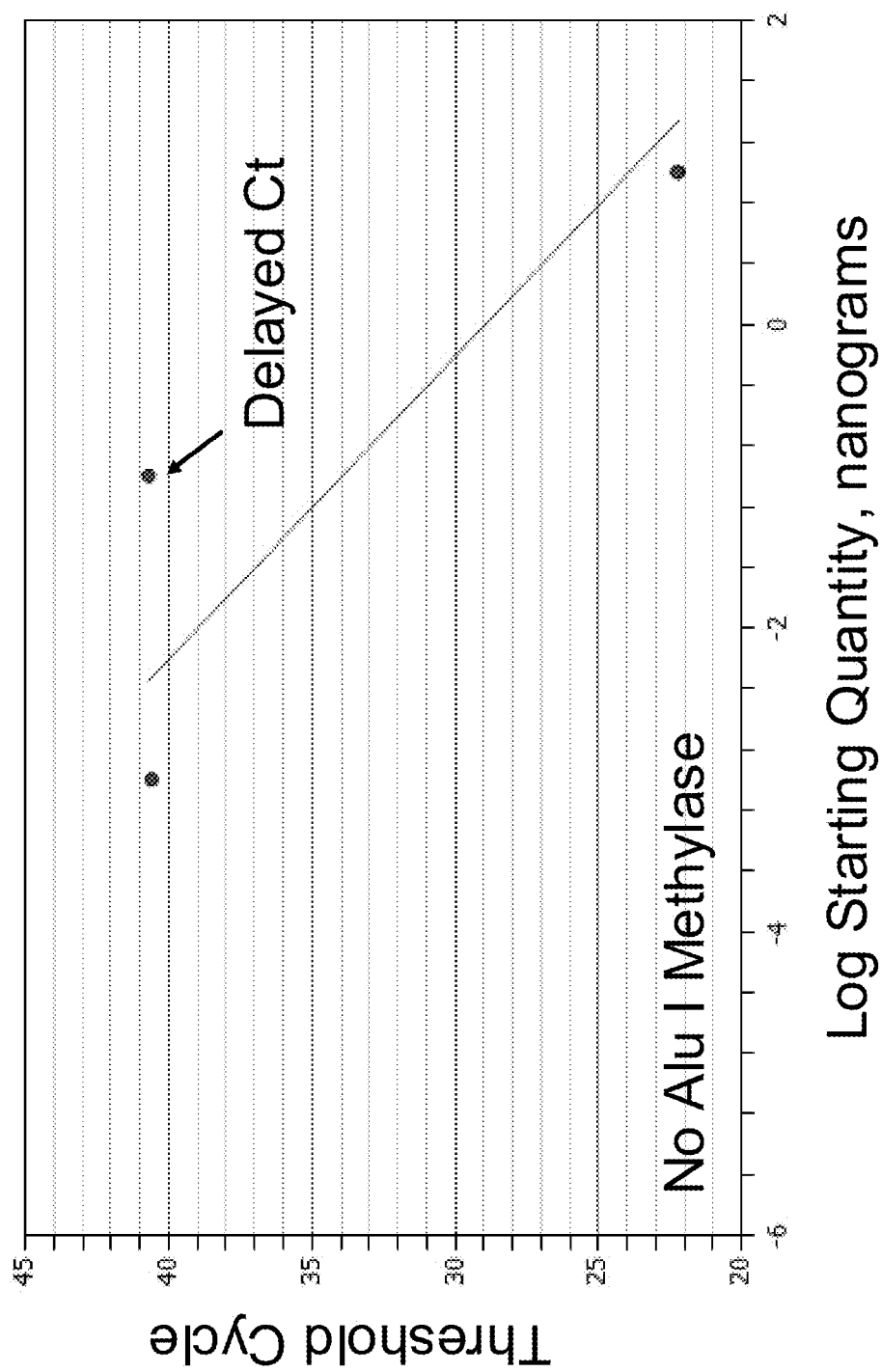
Figure 2D:
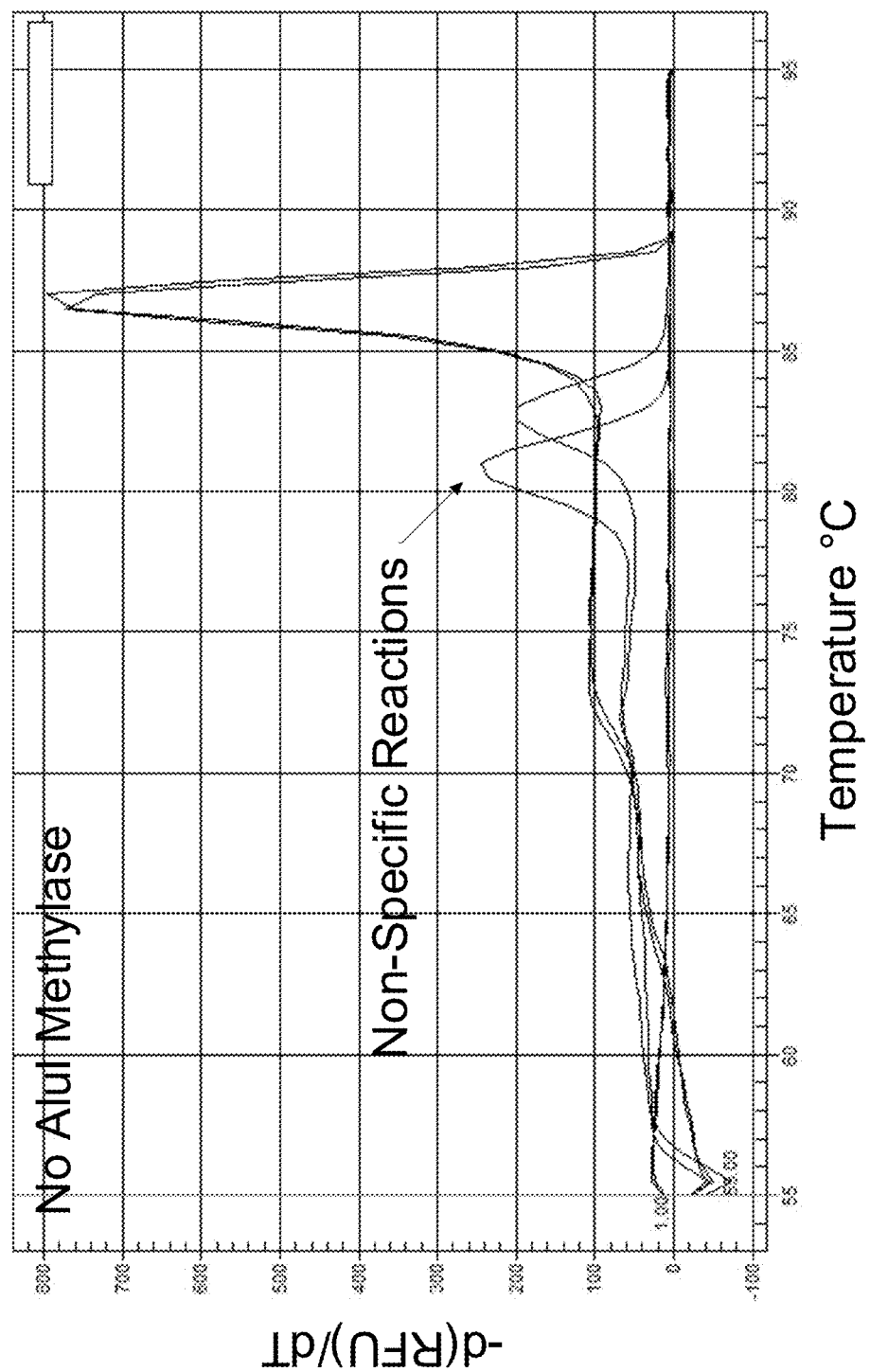
Figure 3A:
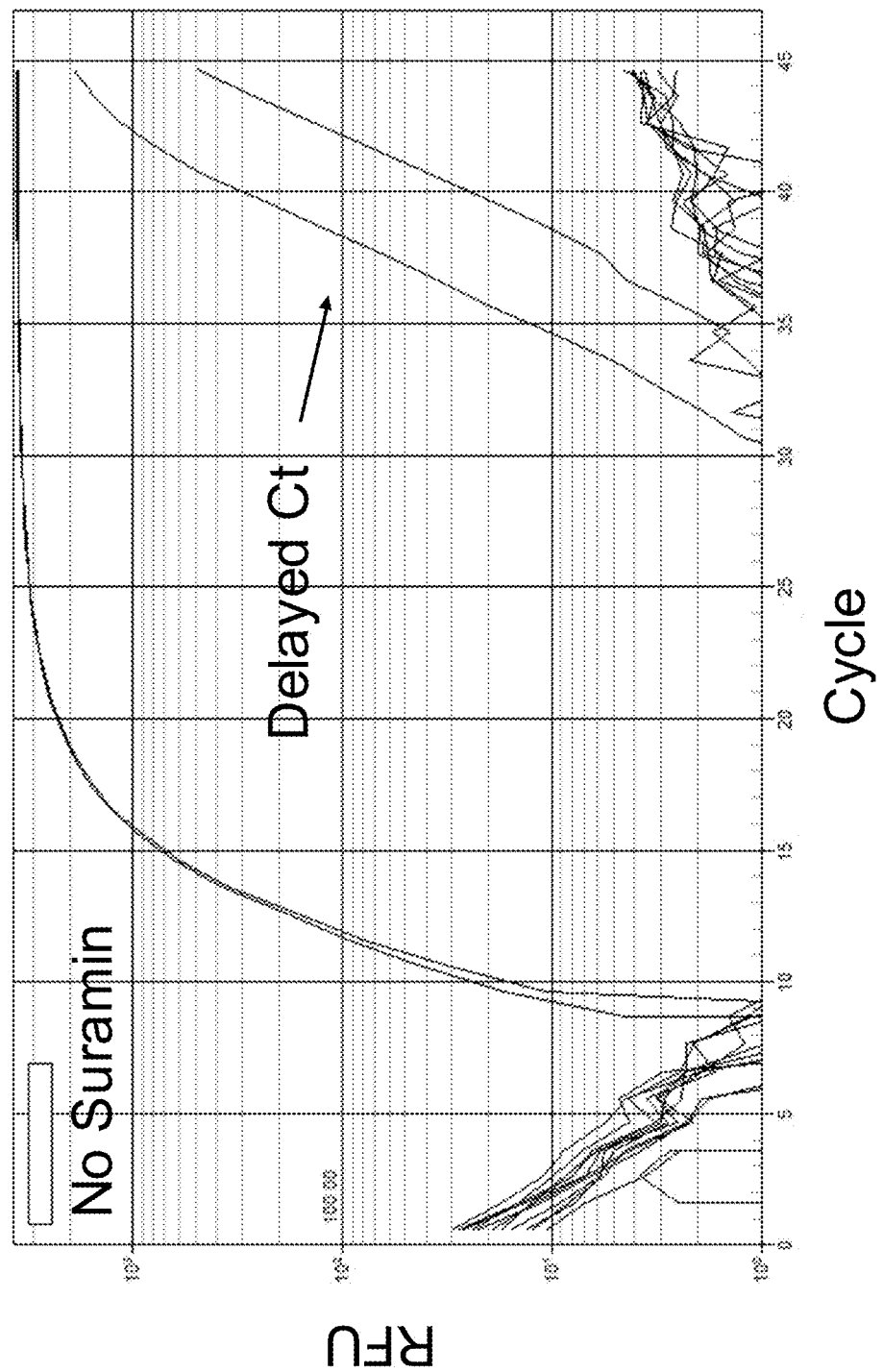
FIGS. 3a-3f show that addition of suramin reduces the inhibition of reverse transcriptase and significantly improves the specificity of one-step RT-PCR.
Figure 3B:
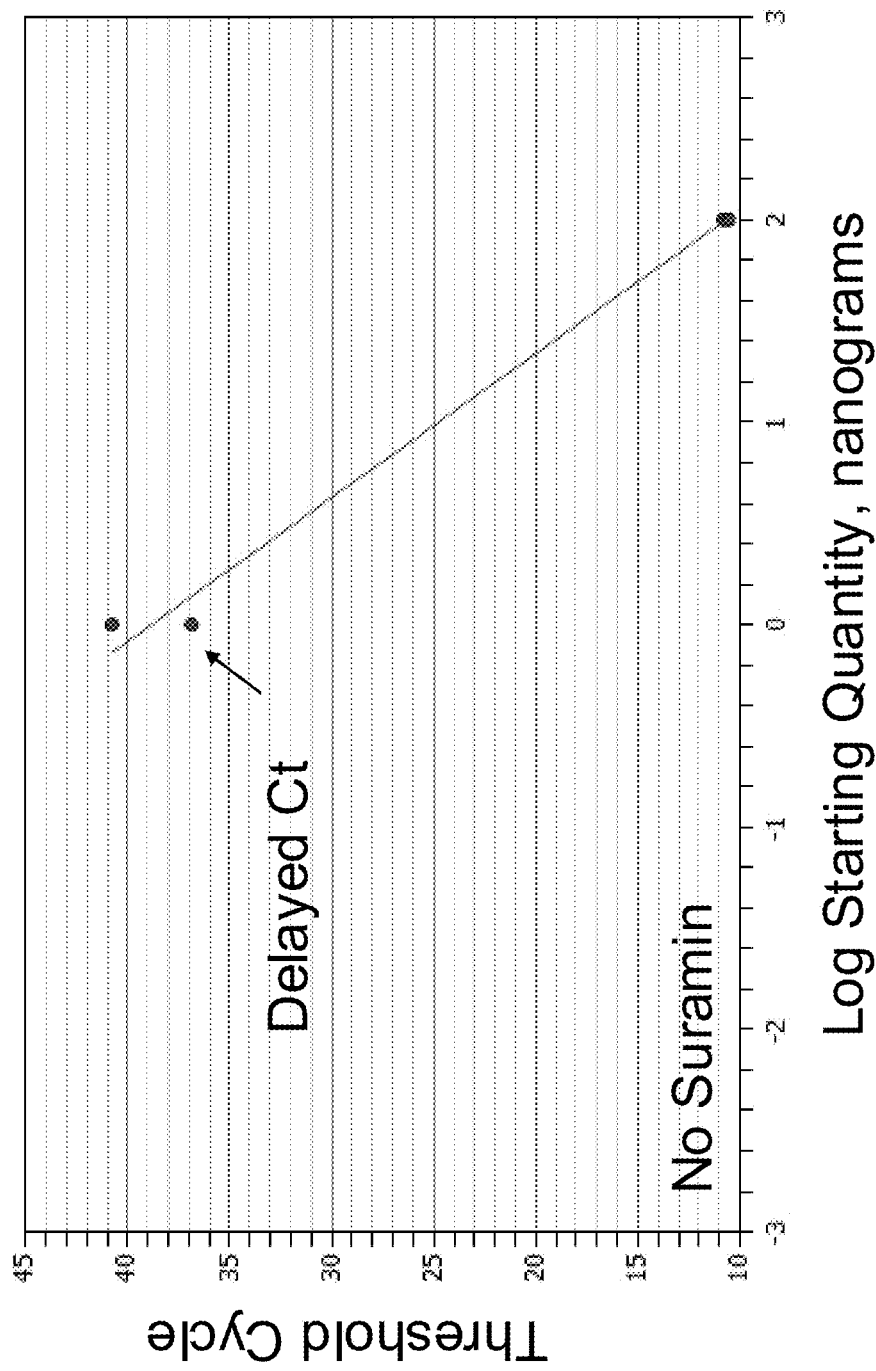
Figure 3C:
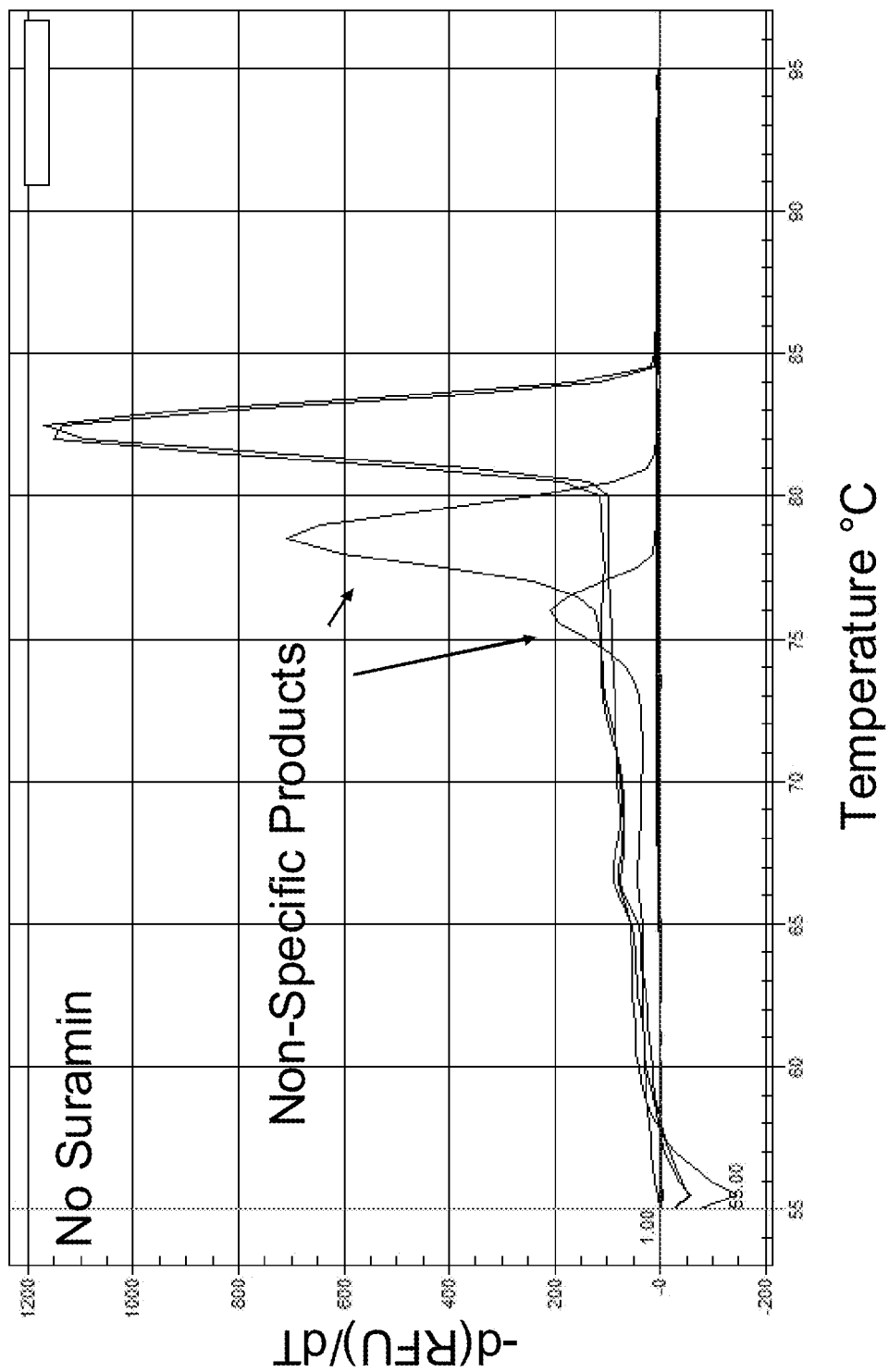
Figure 3D:
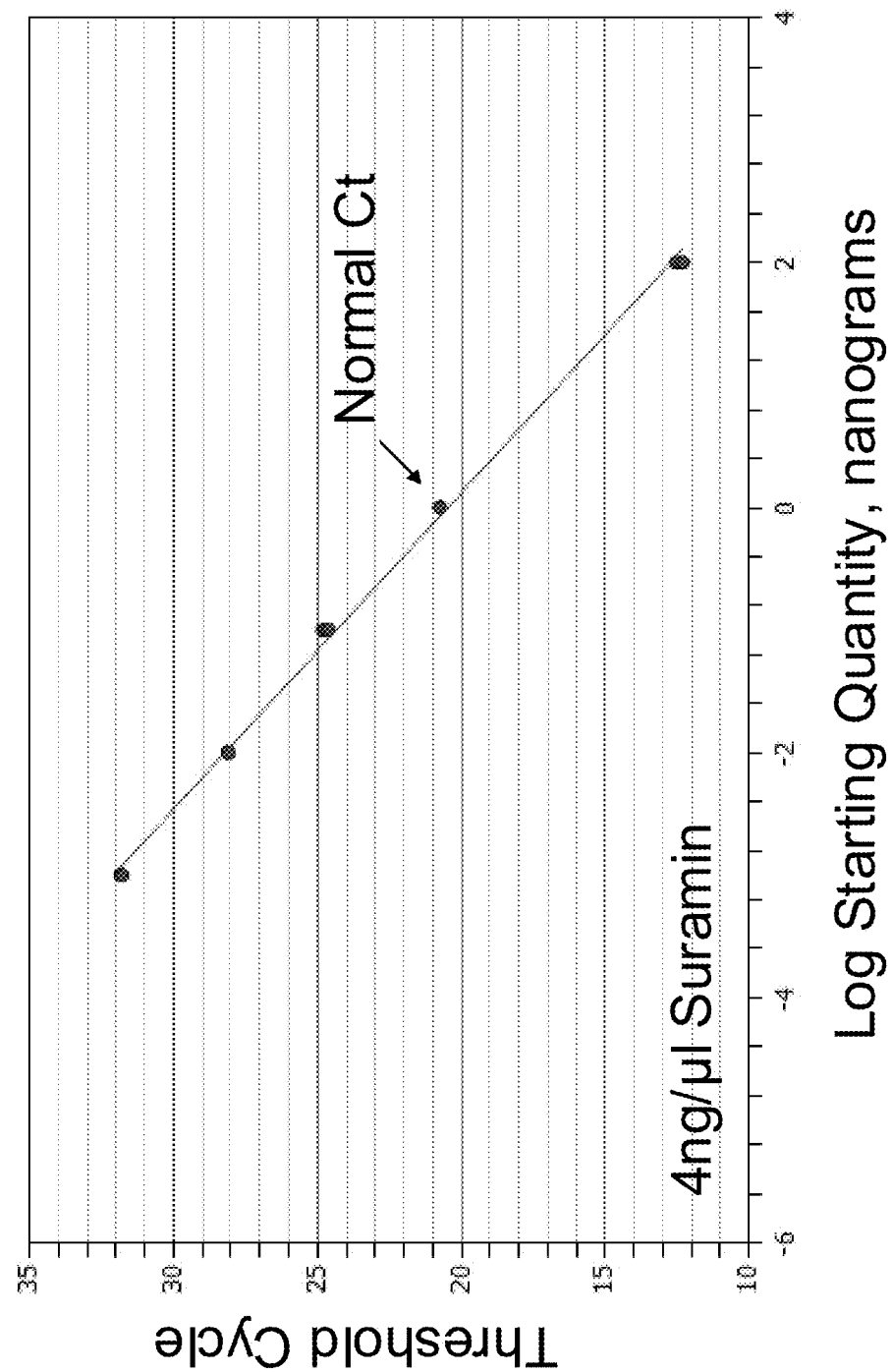
Figure 3E:
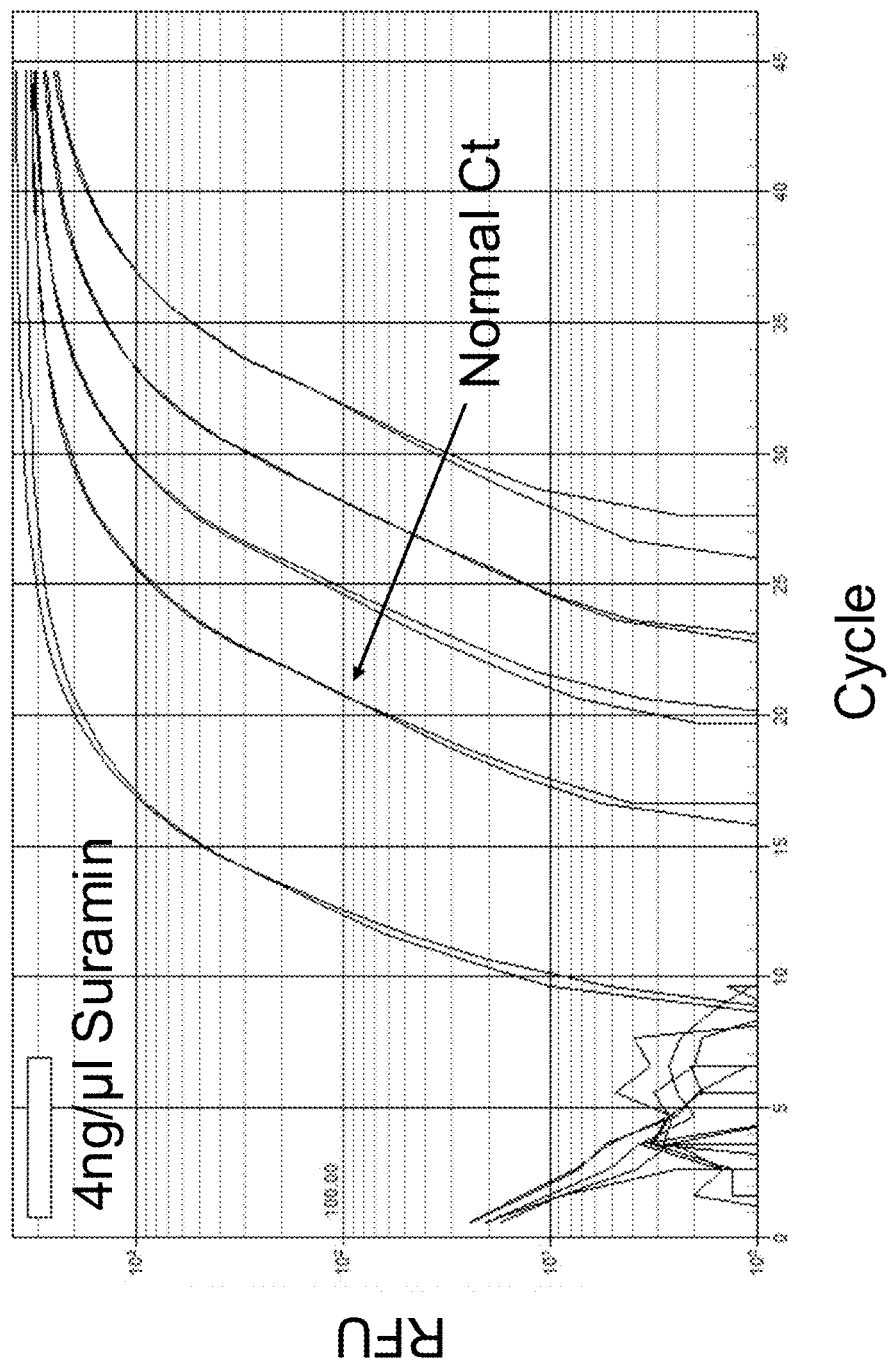
Figure 3F:
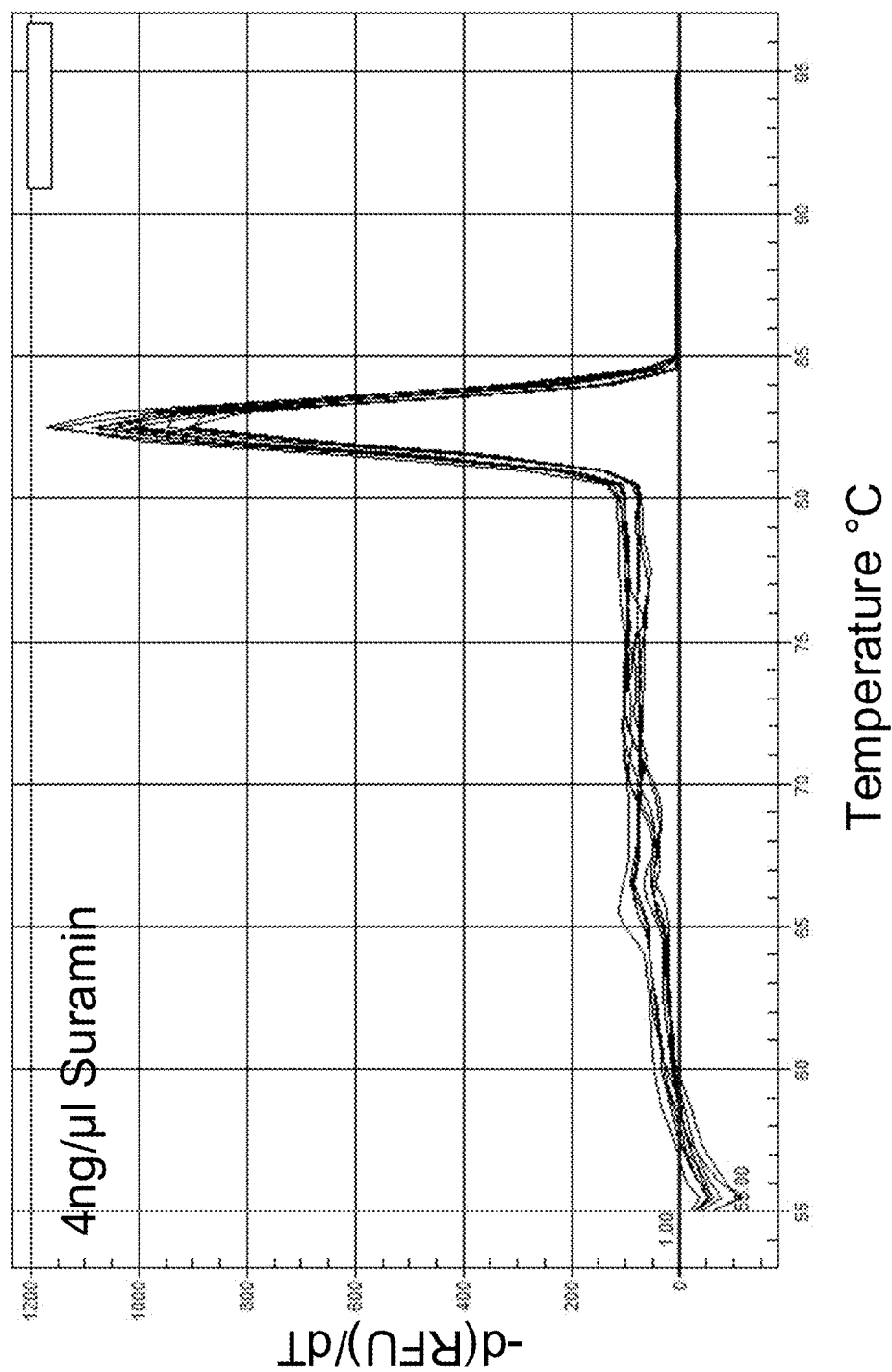
Figure 4A:
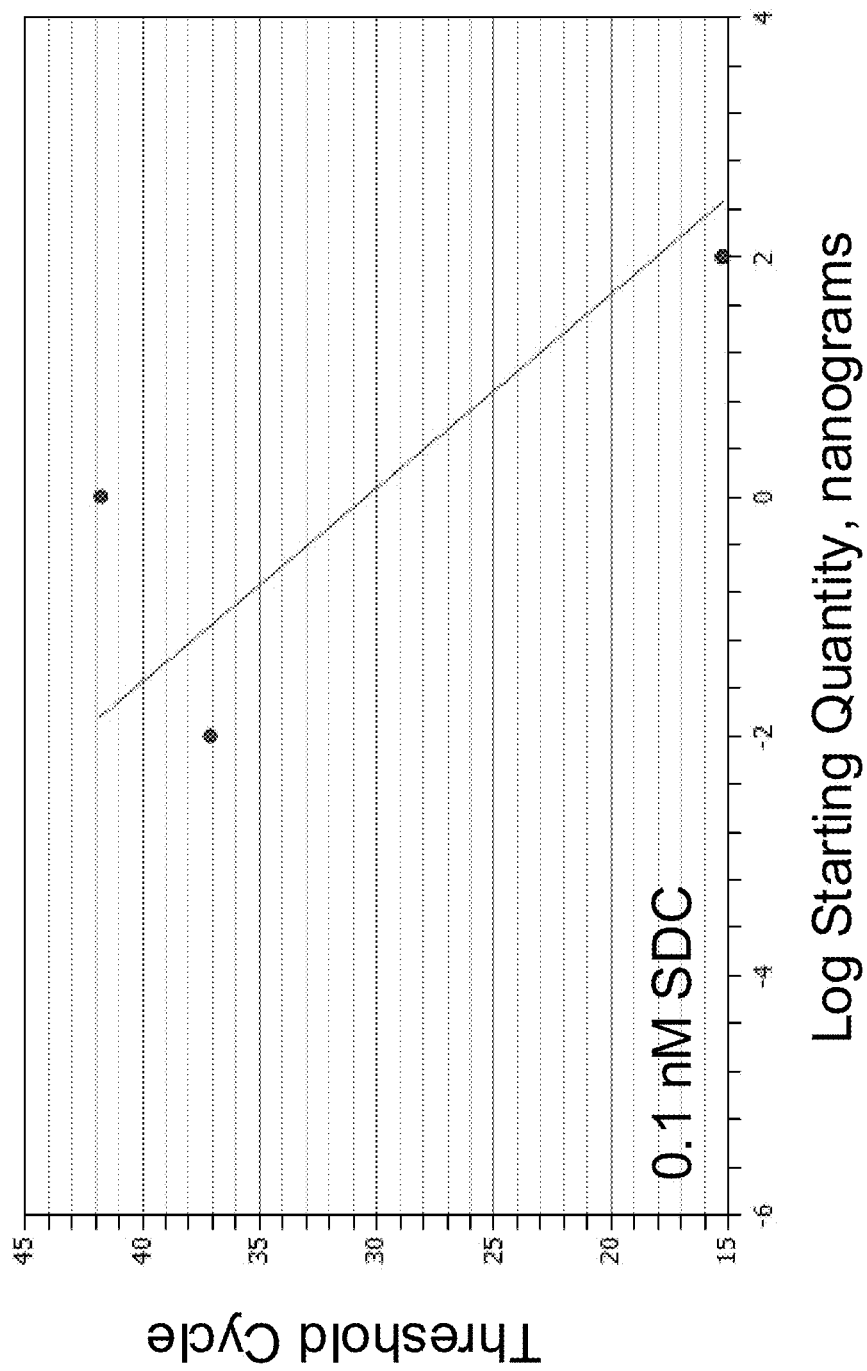
FIGS. 4a-4h shows that addition of phosphorothioate oligodeoxycytosine (SdC) reduces the inhibition of reverse transcriptase and significantly improves the specificity of one-step RT-PCR.
Figure 4B:
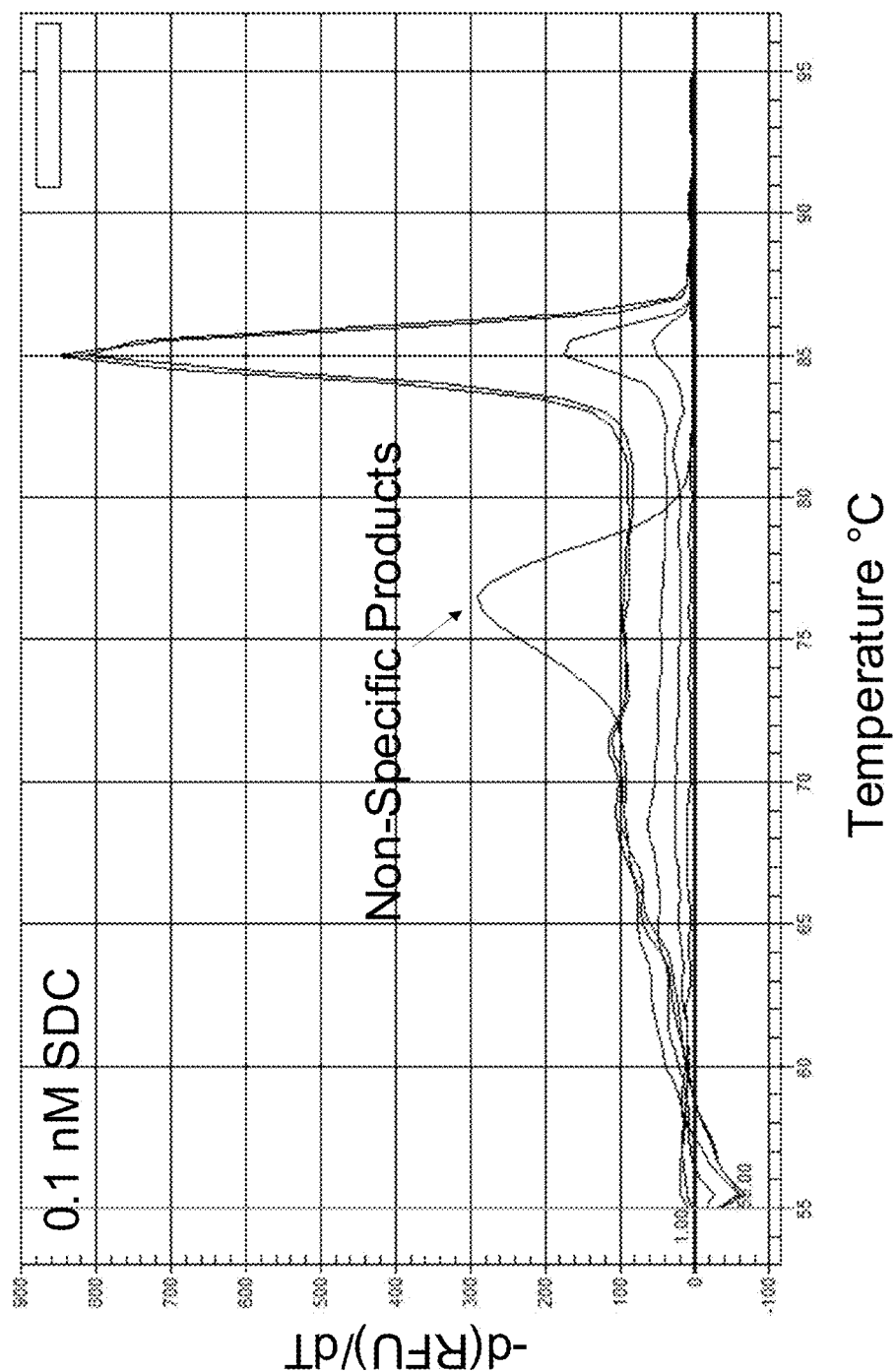
Figure 4C:
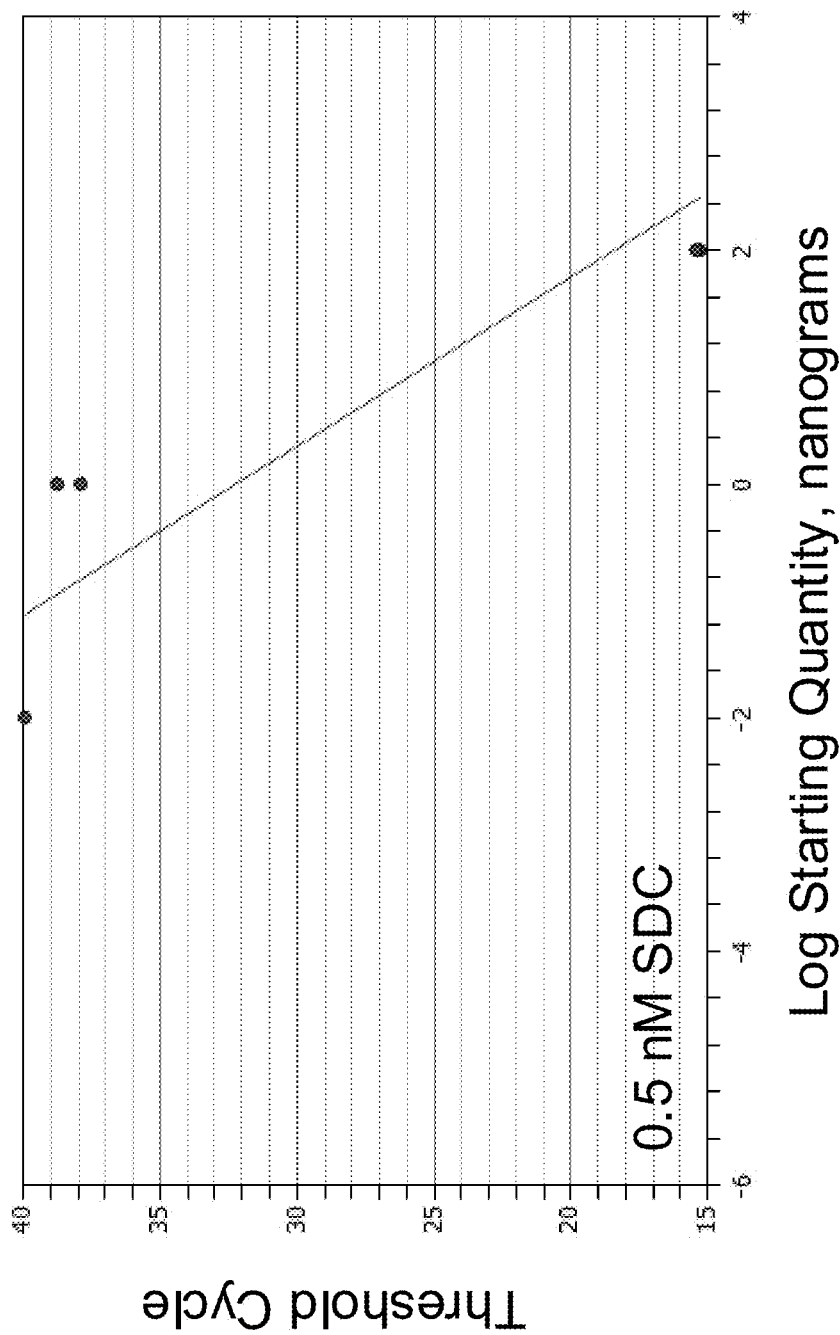
Figure 4D:
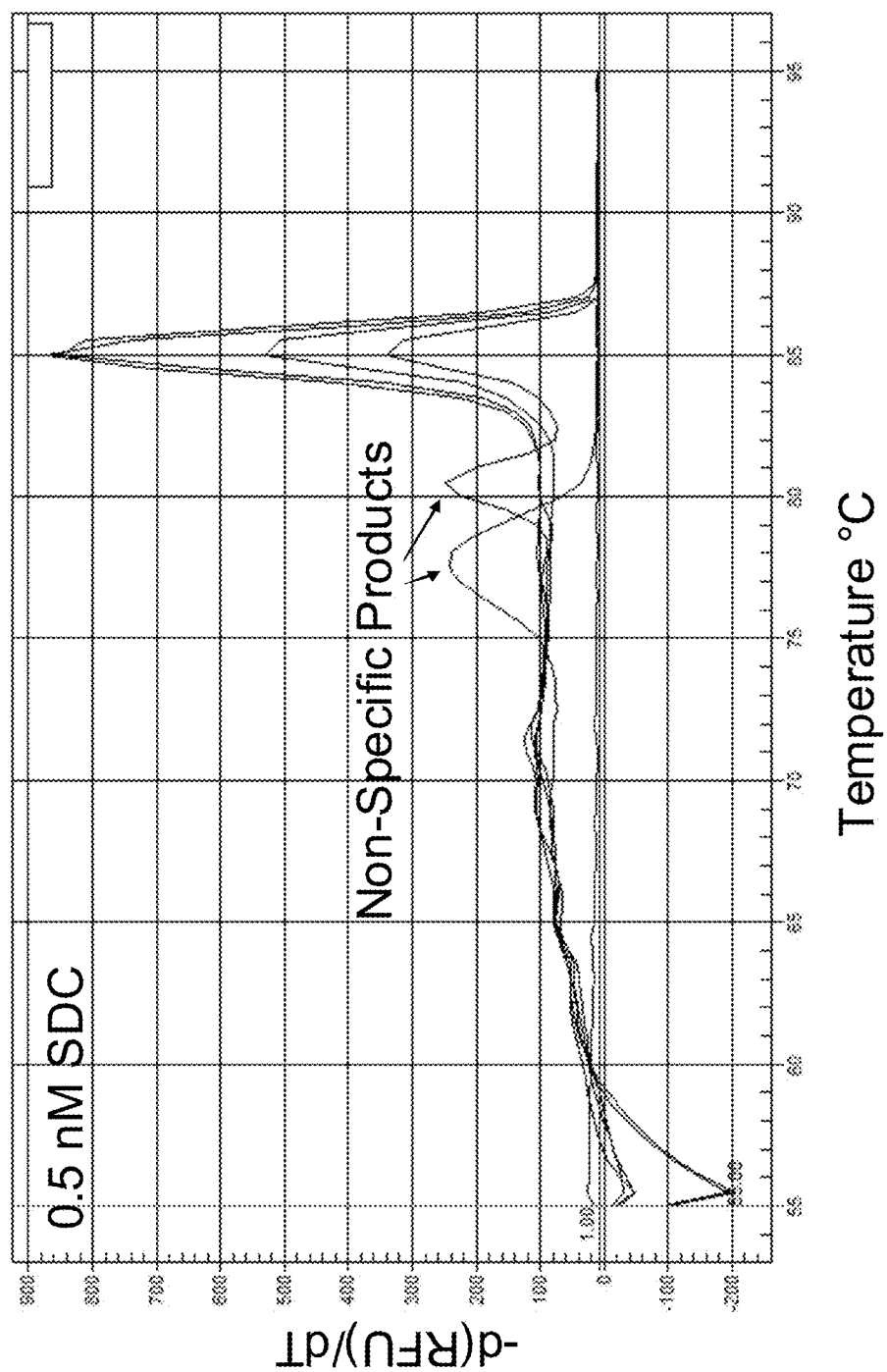
Figure 4E:
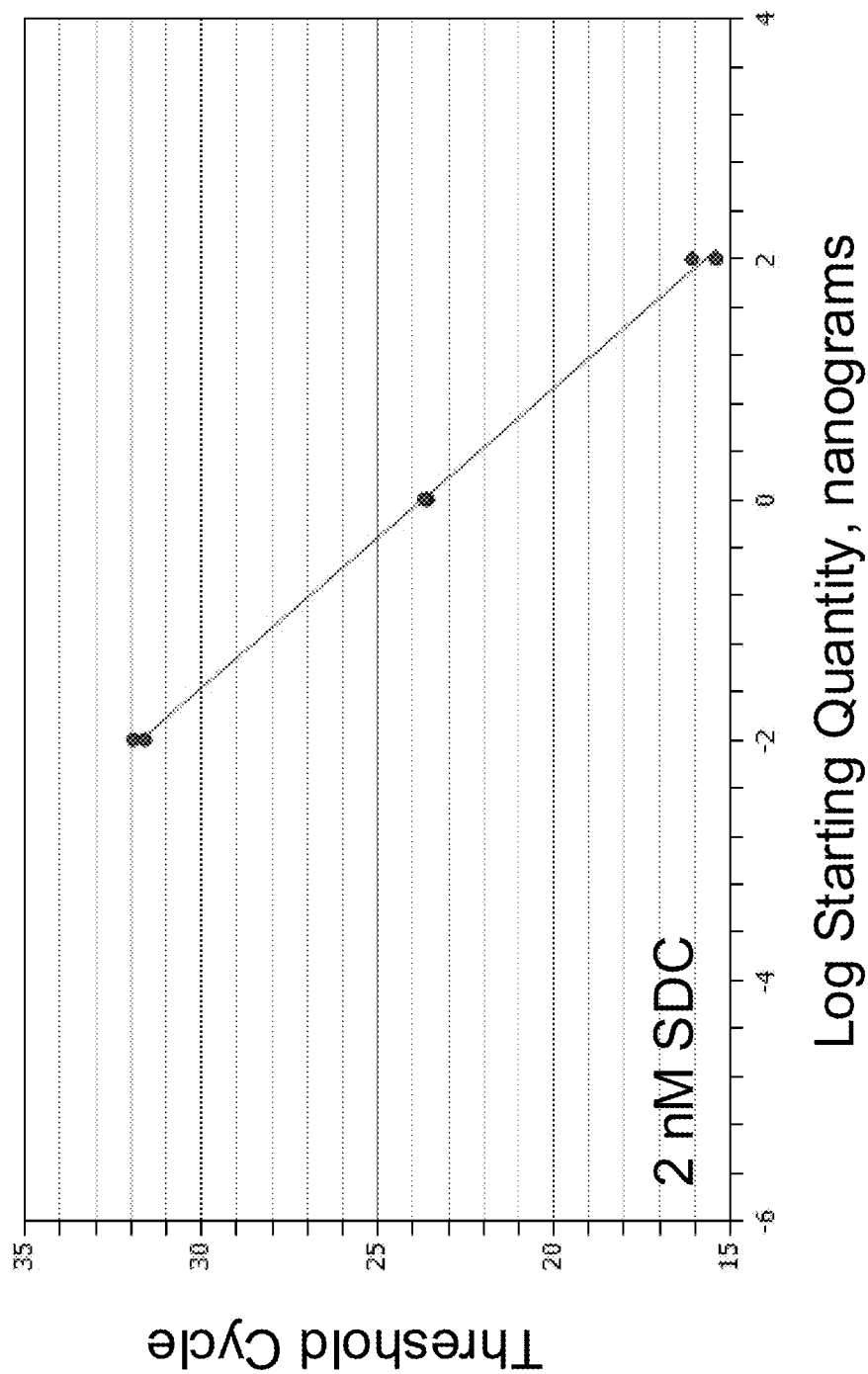
Figure 4F:
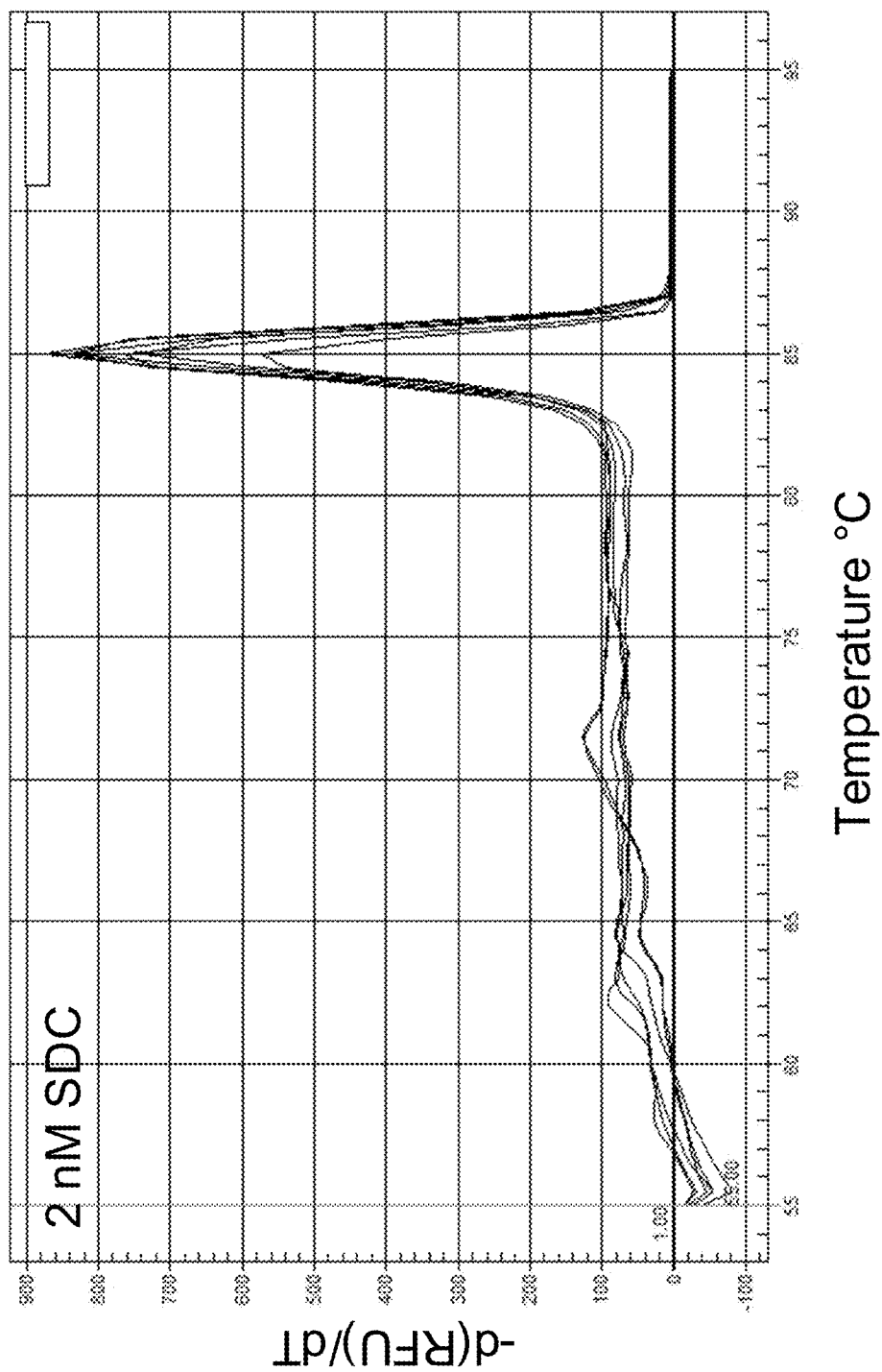
Figure 4G:
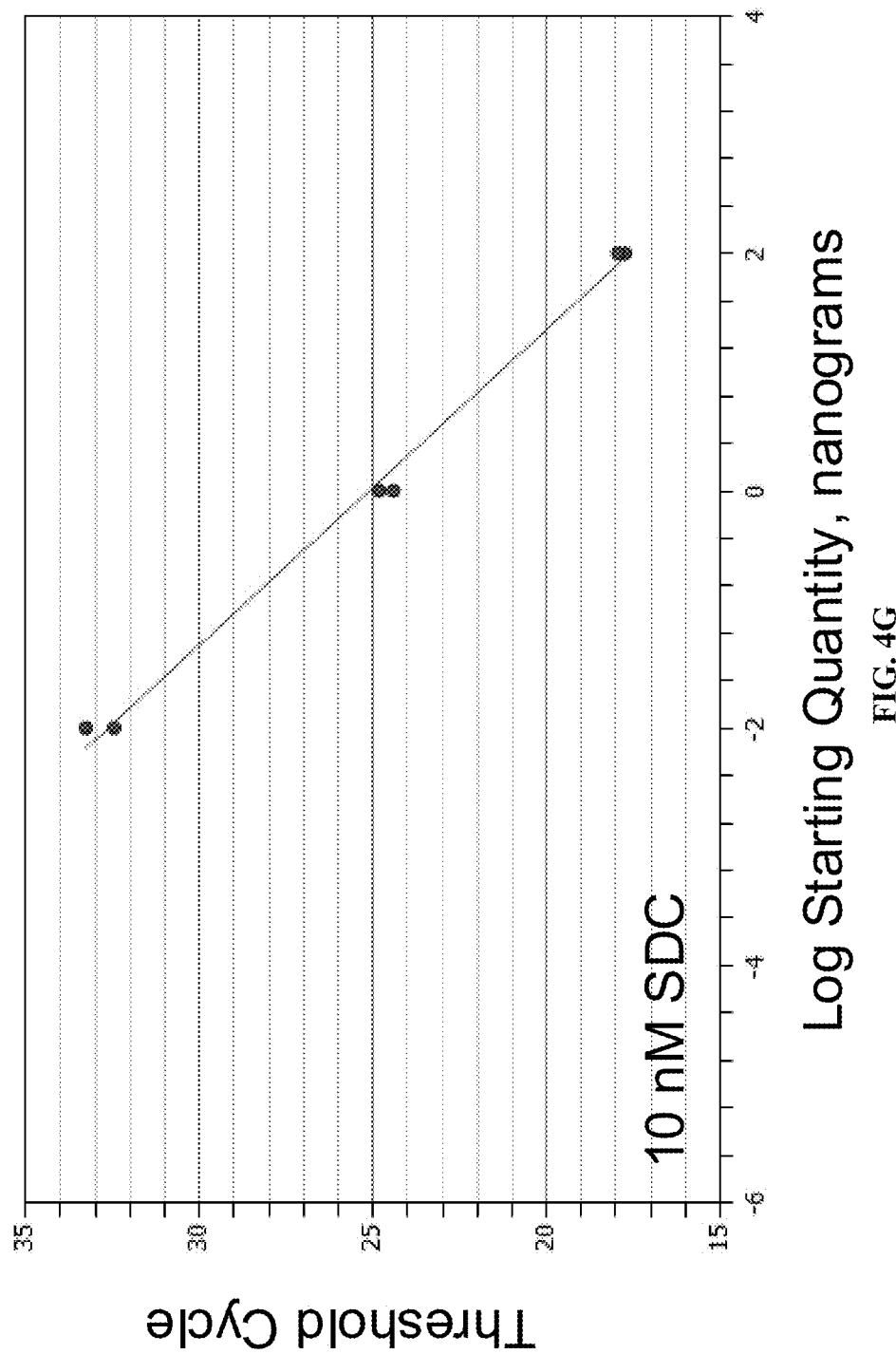
Figure 4H:
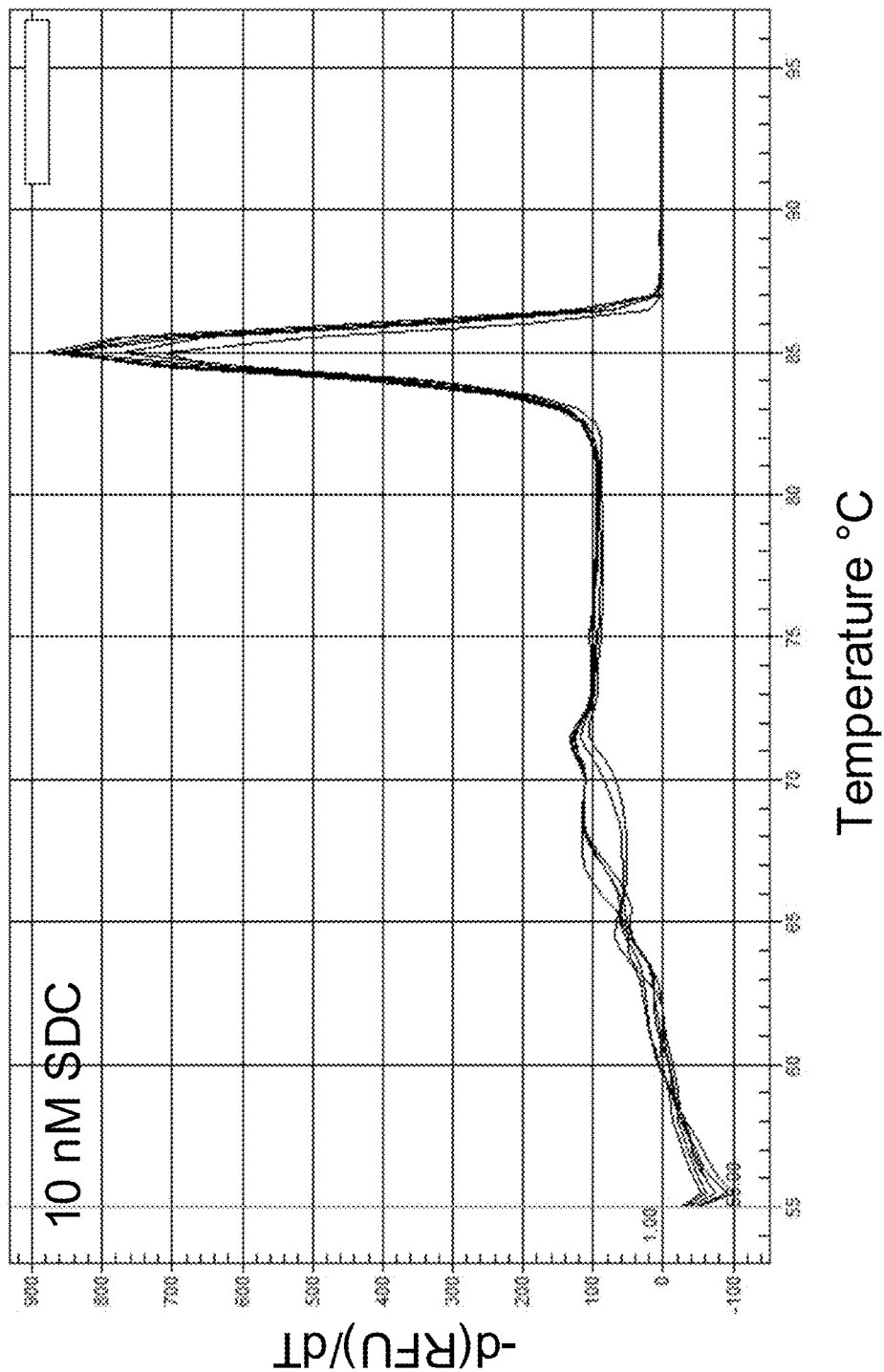
Figure 5A:
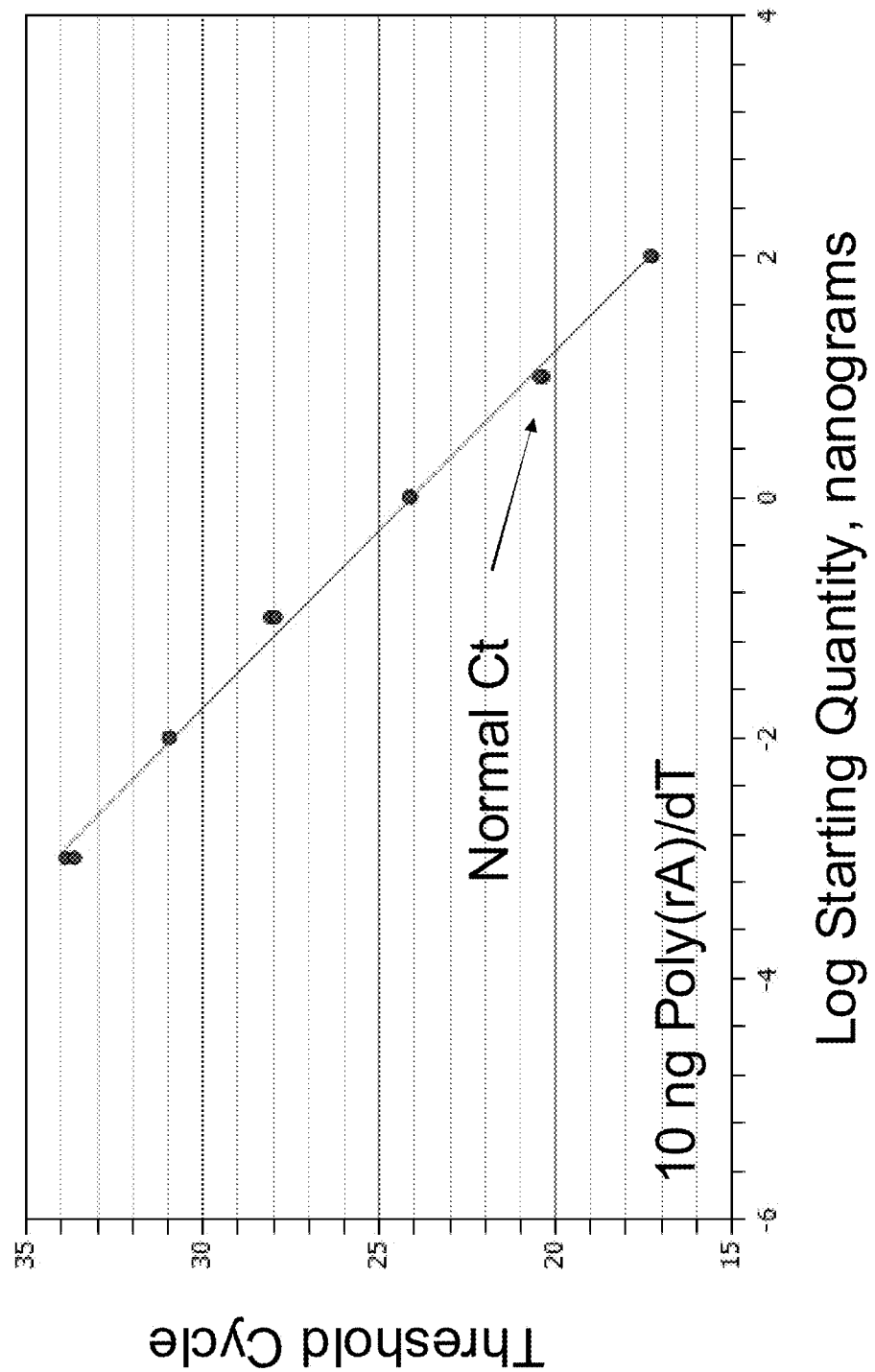
FIGS. 5a-5d show that addition of poly(rA)(dT) reduces the inhibition of reverse transcriptase and significantly improves the specificity of one-step RT-PCR.
Figure 5B:
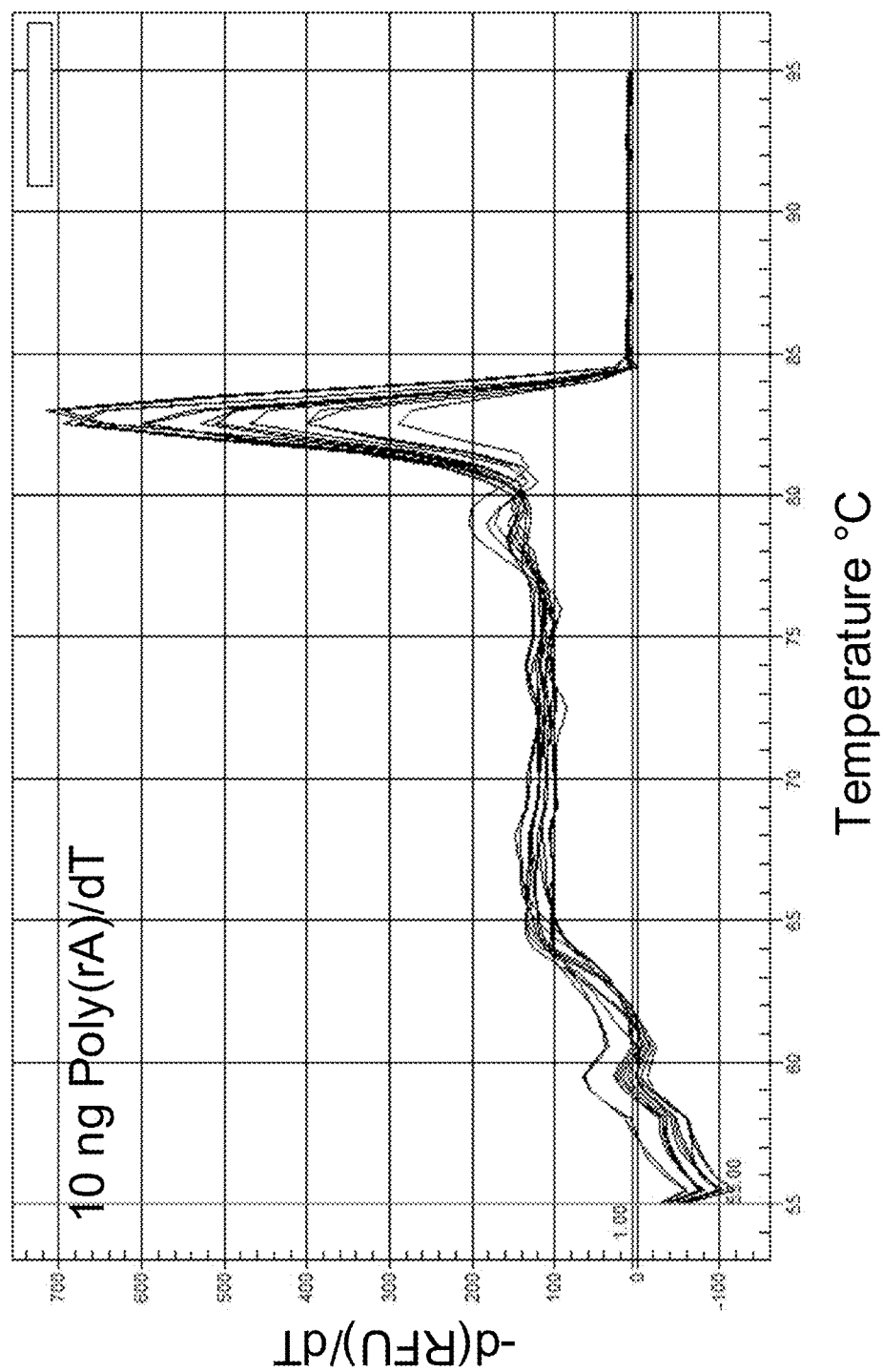
Figure 5C:
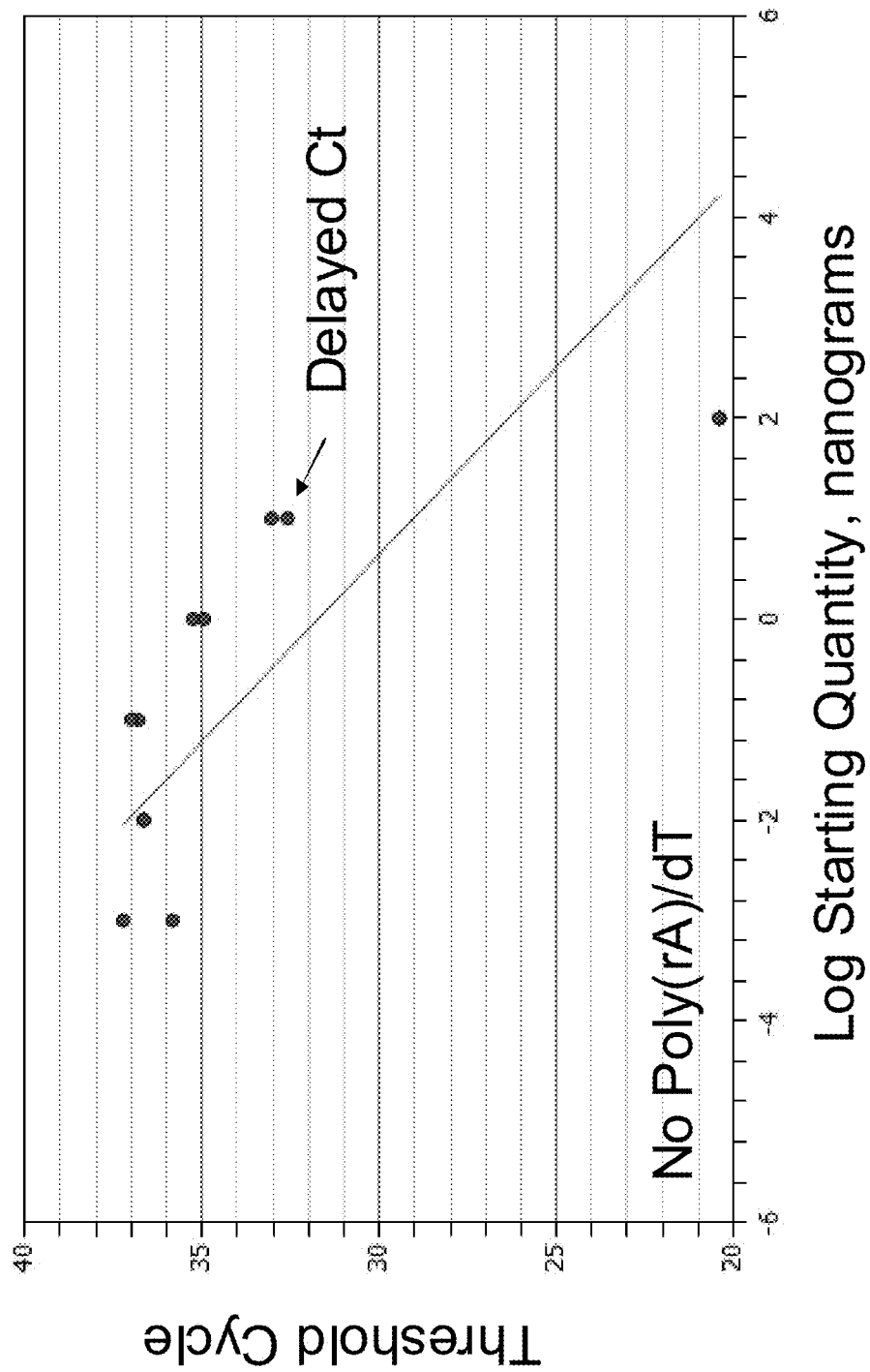
Figure 5D:
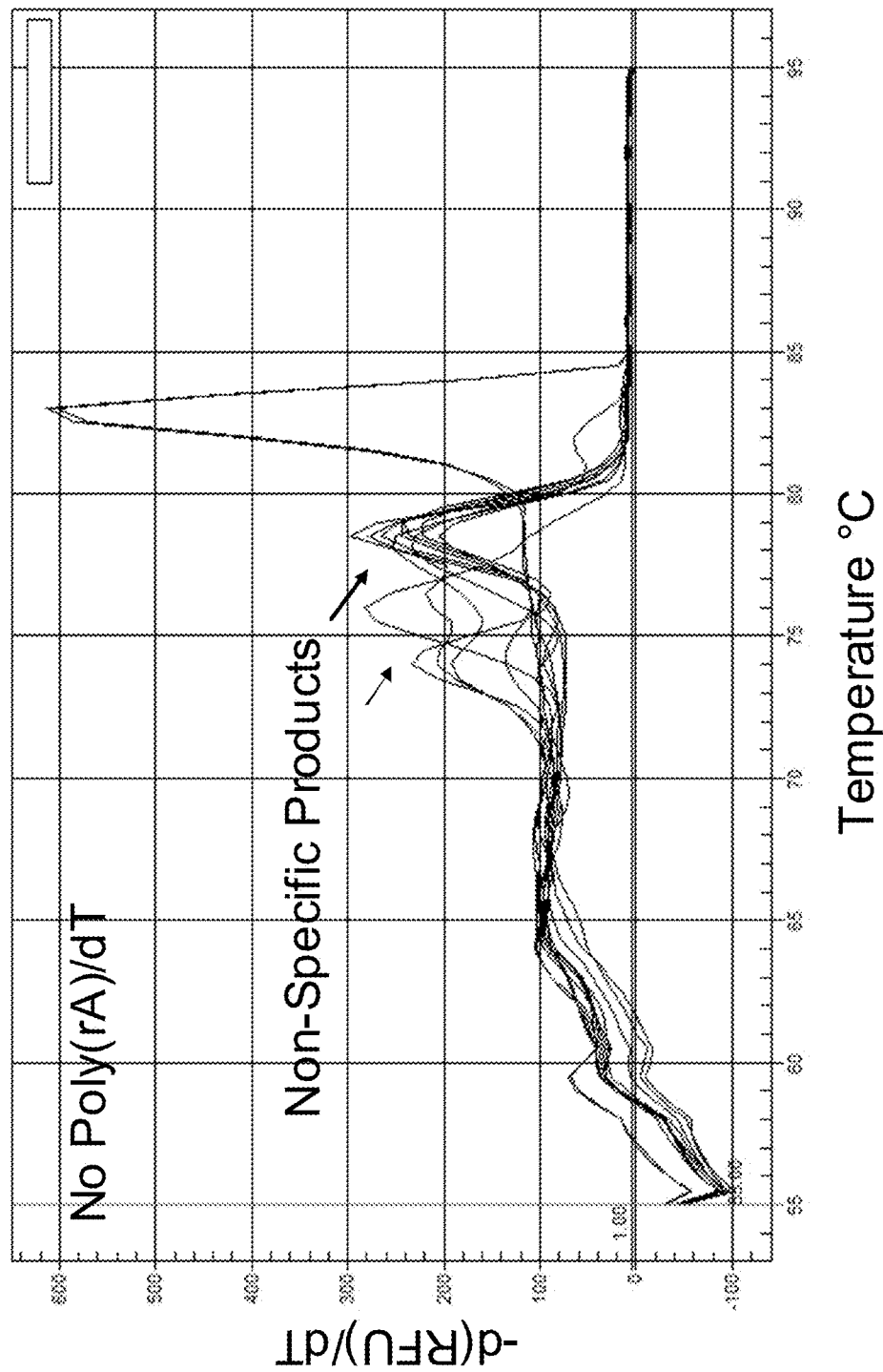

I. Method for Amplifying a Nucleic Acid Molecule

Various techniques for performing quantitative amplification of a nucleic acid are known. These techniques include use of 5' to 3' exonuclease assays, e.g., Taqman™ probes (see, e.g., U.S. Pat. Nos. 5,210,015 and 5,487,972, Heid et al., *Genome Res.* 6:986-994, 1996; Holland et al., *Proc. Nat'l Acad. Sci. USA* 88:7276-7280, 1991; and Lee et al., *Nuc. Acids Res.* 21:3761-3766, 1993). Other methodologies employ one or more probe oligonucleotides that are structured such that a change in fluorescence is generated when the oligonucleotide(s) is hybridized to a target nucleic acid. For example, one such method involves a dual fluorophore approach that exploits fluorescence resonance energy transfer (FRET), e.g., LightCycler™ hybridization probes, where two oligo probes anneal to the amplicon (e.g. U.S. Pat. No. 6,174,670). The oligonucleotides are designed to hybridize in a head-to-tail orientation with the fluorophores separated at a distance that is compatible with efficient energy transfer. Other examples of labeled oligonucleotides that are structured to emit a signal when bound to a nucleic acid or incorporated into an extension product include: Scorpions™ probes (e.g., Whitcombe et al., *Nature Biotechnology* 17:804-807, 1999, and U.S. Pat. No. 6,326,145), Sunrise (or Ampliflour™) primers (e.g., Nazarenko et al., *Nuc. Acids Res.* 25:2516-2521, 1997, and U.S. Pat. No. 6,117,635), LUX™ primers and Molecular Beacons™ probes (e.g., Tyagi et al., *Nature Biotechnology* 14:303-308, 1996 and U.S. Pat. No. 5,989,823).

The present invention provides a method for amplifying a nucleic acid molecule. The method involves mixing an RNA template with a composition having a reverse transcriptase, a DNA polymerase and a RT inhibition reducer. The RT inhibition reducer can be Sso7d, Sac7d, Sac7e, Sso7e, AluI methylase, suramin, a phosphorothioate oligodeoxycytosine, a phosphorothioate oligodeoxyadenine, a phosphorothioate oligodeoxythymine and poly(rA)(dT). The mixing forms a mixture that is incubated under conditions sufficient to synthesize a DNA molecule complementary to all or a portion of the RNA template, thereby amplifying the nucleic acid molecule.

In RT-PCR, the reaction mixture is first incubated (in an appropriate buffering agent) at a temperature sufficient to allow synthesis of a DNA molecule complementary to at least a portion of an RNA template. Components of a reverse transcription reaction mixture typically include an RNA template and a DNA primer (oligo dT, random hexamer, or gene-specific primer) from which the complementary DNA (cDNA) is produced; a nucleic acid polymerase that exhibits reverse transcriptase activity; and the appropriate nucleotide building blocks needed for nucleic acid synthesis. For the purposes of this invention, cDNA is defined as any DNA molecule whose nucleic acid sequence is complementary to an RNA molecule. An RNA template is defined as any RNA molecule used to provide a nucleic acid sequence from which a cDNA molecule can be synthesized. The synthesis of cDNA from an RNA template is typically accomplished by utilizing a nucleic acid polymerase that exhibits reverse transcriptase activity. For the purposes of this invention, reverse transcriptase activity refers to the ability of an enzyme to polymerize a cDNA molecule from an RNA template, and reverse transcriptase broadly refers to any enzyme possessing reverse transcriptase activity. Reverse transcription typically occurs in a temperature range from about 20° C. to about 75° C., preferably from about 35° C. to about 70° C.

After reverse transcription of an RNA template to produce a cDNA molecule, the cDNA is incubated (in an appropriate buffering agent) under conditions sufficient for replication of the cDNA molecule. The reaction mixture can be the same as that of the previous reverse transcription reaction mixture, as employed in coupled (also called continuous, or one-step) RT-PCR, or the reaction mixture can comprise an aliquot of the previous reverse transcription reaction mixture and can be further modified for nucleic acid replication, as in uncoupled (or two-step) RT-PCR. Components of a replication reaction mixture typically include a nucleic acid template (in this instance the cDNA); DNA primers; a nucleic acid polymerase; and the appropriate nucleotide building blocks needed for nucleic acid synthesis. Nucleic acid replication refers to the polymerization of a nucleic acid whose sequence is determined by, and complementary to, another nucleic acid. DNA replication, as used herein, is synonymous with DNA amplification. Preferably DNA amplification occurs repetitively, thus replicating both strands of the nucleic acid sequence, i.e., DNA complementary to the RNA template, and DNA whose nucleic acid sequence is substantially identical to the RNA template. Repetitive, or cyclic, DNA replication can be advantageously accomplished using a thermostable polymerase in a Polymerase Chain Reaction (PCR).

PCR is a technique well known in the art. PCR is used to amplify nucleic acids by subjecting a reaction mixture to cycles of: (i) nucleic acid denaturation, (ii) oligonucleotide primer annealization, and (iii) nucleic acid polymerization. Preferred reaction conditions for amplification comprise thermocycling, i.e., alternating the temperature of the reaction mixture to facilitate each of the steps of the PCR cycle. PCR is typically extended through multiple cycles of denaturation, annealization and replication, augmented (optionally and preferably) with an initial prolonged denaturation step and a final prolonged extension (polymerization) step. Thermocycling typically occurs within a temperature range of between about 23° C. to about 100° C., and preferably between about 37° C. to about 95° C. Nucleic acid denaturation typically occurs between about 90° C. to about 100° C., preferably about 94° C. Annealization typically occurs between about 37° C. to about 75° C. preferably about 60° C. Polymerization typically occurs between about 55° C. to about 80° C., preferably about 72° C. The number of thermocycles varies immensely, depending upon practitioner preference, the quantity of DNA template used, and the quantity of DNA product desired. Preferably, the number of PCR cycles ranges from about 5 to about 99, more preferably greater than about 20 cycles, most preferably about 40 cycles.

Primers should be designed according to standard PCR guidelines with a length of 18 to 25 nucleotides, and a GC content of 40% to 65%. Primer design should avoid internal secondary structure, and complementarity at the 3' ends within each primer and primer pair. Optimal results can require titration of primer concentration between 100 and 500 nM. A final concentration of 300 nM per primer is effective for most reactions. In general, reaction efficiency and/or specificity can be optimized using equal concentrations of each primer. For best results, amplicon size should be limited to 50-200 by for quantitative RT-PCR.

Suggested input quantities of template are: 0.1 pg to 100 ng total RNA; 10 fg to 100 ng polyA(+) RNA. First strand synthesis can be performed between 40° C. and 52° C. Optimal results are generally obtained with a 10-minute incubation at 50° C.

A. RNA Template

The template RNA can be any ribonucleic acid of interest, known or unknown to the practitioner. Template RNA can be artificially synthesized or isolated from natural sources. In some embodiments, the RNA template can be a ribonucleic acid such as RNA, mRNA, piRNA, tRNA, rRNA, ncRNA, gRNA, shRNA, siRNA, snRNA, miRNA and snoRNA. Preferably the RNA is mRNA. More preferably the RNA is biologically active or encodes a biologically active polypeptide.

The RNA template can be present in any useful amount. In some embodiments, the RNA template concentration is 50 pg/µL or less. One of skill in the art will appreciate that other RNA template concentrations are useful in the present invention.

B. Reverse Transcriptase

Reverse transcriptases useful in the present invention can be any polymerase that exhibits reverse transcriptase activity. Preferred enzymes include those that exhibit reduced RNase H activity. Several reverse transcriptases are known in the art and are commercially available (e.g., from Boehringer Mannheim Corp., Indianapolis, Ind.; Life Technologies, Inc., Rockville, Md.; New England Biolabs, Inc., Beverley, Mass.; Perkin Elmer Corp., Norwalk, Conn.; Pharmacia LKB Biotechnology, Inc., Piscataway, N.J.; Qiagen, Inc., Valencia, Calif.; Stratagene, La Jolla, Calif.). In some embodiments, the reverse transcriptase can be Avian Myeloblastosis Virus reverse transcriptase (AMV-RT), Moloney Murine Leukemia Virus reverse transcriptase (M-MLV-RT), Human Immunovirus reverse transcriptase (HIV-RT), EIAV-RT, RAV2-RT, C. hydrogenoformans DNA Polymerase, rTth DNA polymerase, SUPERSCRIPT I, SUPERSCRIPT II, and mutants, variants and derivatives thereof. It is to be understood that a variety of reverse transcriptases can be used in the present invention, including reverse transcriptases not specifically disclosed above, without departing from the scope or preferred embodiments thereof. In some other embodiments, the reverse transcriptase is M-MLV reverse transcriptase.

C. DNA Polymerase

DNA polymerases useful in the present invention can be any polymerase capable of replicating a DNA molecule. Preferred DNA polymerases are thermostable polymerases, which are especially useful in PCR. Thermostable polymerases are isolated from a wide variety of thermophilic bacteria, such as *Thermus aquaticus* (Taq), *Thermus brockianus* (Tbr), *Thermus flavus* (Tfl), *Thermus ruber* (Tru), *Thermus thermophilus* (Tth), *Thermococcus litoralis* (Tli) and other species of the *Thermococcus* genus, *Thermoplasma acidophilum* (Tac), *Thermotoga neapolitana* (Tne), *Thermotoga maritima* (Tma), and other species of the *Thermotoga* genus, *Pyrococcus furiosus* (Pfu), *Pyrococcus woesei* (Pwo) and other species of the *Pyrococcus* genus, *Bacillus sterothermophilus* (Bst), *Sulfolobus acidocaldarius* (Sac) *Sulfolobus solfataricus* (Sso), *Pyrodictium occultum* (Poc), *Pyrodictium abyssi* (Pab), and *Methanobacterium thermoautotrophicum* (Mth), and mutants, variants or derivatives thereof.

Several DNA polymerases are known in the art and are commercially available (e.g., from Boehringer Mannheim Corp., Indianapolis, Ind.; Life Technologies, Inc., Rockville, Md.; New England Biolabs, Inc., Beverley, Mass.; Perkin Elmer Corp., Norwalk, Conn.; Pharmacia LKB Biotechnology, Inc., Piscataway, N.J.; Qiagen, Inc., Valencia, Calif.; Stratagene, La Jolla, Calif.). In some embodiments, the DNA polymerase can be Taq, Tbr, Tfl, Tru, Tth, Tli, Tac, Tne, Tma, Tih, Tfi, Pfu, Pwo, Kod, Bst, Sac, Sso, Poc, Pab, Mth, Pho, ES4, VENT™, DEEPVENT™, and active mutants, variants and derivatives thereof. It is to be understood that a variety of DNA polymerases can be used in the present invention, including DNA polymerases not specifically disclosed above, without departing from the scope or preferred embodiments thereof. In some other embodiments, the DNA polymerase is Taq DNA polymerase. One of skill in the art will appreciate that other DNA polymerases are useful in the present invention.

Other DNA polymerases useful in the method of the present invention include, but are not limited to, thermophilic DNA polymerases.

The reverse transcriptase can be present in any appropriate ratio to the DNA polymerase. In some embodiments, the ratio of reverse transcriptase to DNA polymerase in unit activity is greater than or equal to 3. One of skill in the art will appreciate that other reverse transcriptase to DNA polymerase ratios are useful in the present invention.

D. RT Inhibition Reducer

The RT inhibition reducer can be any moiety that reduces reverse transcriptase inhibition in RT-PCR. In some embodiments, the present invention provides a RT inhibition reducer that can be Sso7d, Sac7d, Sac7e, Sso7e, AluI methylase, suramin, a phosphorothioate oligodeoxycytosine, a phosphorothioate oligodeoxyadenine, a phosphorothioate oligodeoxythymine and poly(rA)(dT). One of skill in the art will appreciate that other RT inhibition reducers are useful in the present invention.

In some embodiments, the RT inhibition reducer is a sequence non-specific double stranded DNA binding protein. The sequence non-specific double stranded DNA binding protein is functional at any temperature. In other embodiments, the sequence non-specific double stranded DNA binding protein is functional below 70° C. In some other embodiments, the sequence non-specific double stranded DNA binding protein is functional below 55° C.

In another embodiment, the sequence non-specific double stranded DNA binding protein can be a DNA modification enzyme including, but not limited to, methylases such as AluI methylase, double strand DNA-specific nucleases or recombinases. The DNA modification enzymes useful in the method of the present invention have reduced or no enzymatic activity but maintain their ability to bind to the dsDNA substrate.

In other embodiments, the sequence non-specific double stranded DNA binding protein can be Sso7d, Sac7d, Sac7e or Sso7e. One of skill in the art will appreciate that other sequence non-specific double stranded DNA binding proteins are useful in the present invention.

In a further embodiment, the present invention provides a sulfonic-acid molecule as the RT inhibition reducer. In some embodiments, the sulfonic-acid molecule can be a sulfonic-acid salt such as ammonium sulfate, magnesium sulfate, manganese sulfate, potassium sulfate and sodium sulfate. In other embodiments, the sulfonic-acid molecule can be a buffer such as AMPSO (3-[(1,1-dimethyl-2-hydroxyethyl)amino]-2-hydroxy-propanesulfonic acid), BES (N,N-bis[2-hydroxyethyl]-2-aminomethanesulfonic acid), MOPS (3-N-morpholino)-propanesulfonic acid), MOPSO (3-N-morpholino)-2-hydroxypropanesulfonic acid, TES (2-{[tris-(hydroxymethyl)methyl]amino}ethanesulfonic acid), HEPES (N-2-hydroxyethylpiperazine-N'-2-ethansulfonic acid), HEPPS (N-2-hydroxyethylpiperazine-N'-3-propanesulfonic acid), HEPPSO (N-2-hydroxyethylpiperazine-N'-2-hydroxypropanesulfonic acid), TAPS (TES(3-{[tris-(hydroxymethyl)methyl]amino}propanesulfonic acid, CHES (2-(N-cyclo-hexylamino)ethanesulfonic acid), MES (2-N-morpholino)ethanesulfonic acid, PIPES (piperazine-N,N'-bis-2-ethanesulfonic acid), POPSO (piperazine-N,N'-bis[2-hydroxy]propanesulfonic acid), TAPS (N-tris[hydroxymethyl]methyl-3-aminopropanesulfonic acid), TAPSO (3[N-tris{hydroxymethyl}methylamino]-2-hydroxypropanesulfonic acid), ACES (N-2-acetamide-2-aminoethane sulfonic acid), DIPSO (3-[N,N-bis(2-hydroxyethyl)amino]-2-hydroxypropanesulfonic acid), CAPSO (3-[cyclohexylamino]-2-hydroxy-1-propanesulfonic acid) and CAPS (3-[cyclohexylamino]propanesulfonic acid). In still other embodiments, the sulfonic-acid molecule can be suramin. In yet other embodiments, the sulfonic-acid molecule can be a sulfonic-acid polymer. One of skill in the art will appreciate that other sulfonic-acid molecules are useful as the RT inhibition reducer of the present invention.

In other embodiments, the RT inhibition reducer can be a phosphorothioate oligodeoxynucleotide of the formula:

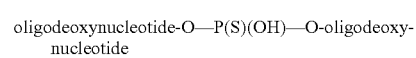

oligodeoxynucleotide-O—P(S)(OH)—O-oligodeoxynucleotide

In some embodiments, the phosphorothioate oligodeoxynucleotide can be a phosphorothioate oligodeoxycytosine (SdC), a phosphorothioate oligodeoxyadenine (SdA), a phosphorothioate oligodeoxythymine (SdT) or a phosphorothioate oligodeoxyguanosine (SdG). In some other embodiments, the RT inhibition reducer can be SdC. The phosphorothioate oligodeoxynucleotides of the present invention can be of any size. The phosphorothioate oligodeoxynucleotides useful in the present invention include, but are not limited to, 10-mers, 12-mers, 14-mers, 16-mers, 18-mers, 20-mers, 22-mers, 24-mers, 26-mers, 28-mers, etc. One of skill in the art will appreciate that other phosphorothioate oligodeoxynucleotides are useful in the present invention.

In a further embodiment, the RT inhibition reducer is a duplex of DNA and RNA comprising an RNA tail. The DNA portion of the duplex can separately be any suitable nucleotide sequence, including homogeneous and heterogeneous sequences including dA, dC, dG and dT in any combination. The DNA portion of the duplex can separately be any suitable nucleotide sequence, including homogeneous and heterogeneous sequences including rA, rC, rG and rT in any combination. In some embodiments, the DNA portion is oligo(dT) and the RNA portion is poly(rA). The RNA tail can be any appropriate tail such as poly(rA), poly(rC), poly(rG) or poly(rT). In other embodiments, the RNA tail is poly(rA).

The RT inhibition reducer can be present in any useful amount. In some embodiments, the RT inhibition reducer is present in an amount from about 0.01 nM to about 1000 nM. In other embodiments, the RT inhibition reducer is present in an amount from about 0.1 nM to about 100 nM. In still other embodiments, the RT inhibition reducer is present in an amount from about 1 nM to about 10 nM. One of skill in the art will appreciate that other amounts of the RT inhibition reducer are useful in the present invention.

E. Primers

In some embodiments, the method of the present invention can include a nucleic acid primer. Oligonucleotide primers useful in the present invention can be any oligonucleotide of two or more nucleotides in length. Preferably, PCR primers are about 15 to about 30 bases in length, and are not palindromic (self-complementary) or complementary to other primers that can be used in the reaction mixture. Primers can be, but are not limited to, random primers, homopolymers, or primers specific to a target RNA template (e.g., a sequence specific primer). Oligonucleotide primers are oligonucleotides used to hybridize to a region of a target nucleic acid to facilitate the polymerization of a complementary nucleic acid. In preferred RT-PCR techniques, primers serve to facilitate reverse transcription of a first nucleic acid molecule complementary to a portion of an RNA template (e.g., a cDNA molecule), and also to facilitate replication of the nucleic acid (e.g., PCR amplification of DNA). Any primer can be synthesized by a practitioner of ordinary skill in the art or can be purchased from any of a number of commercial venders (e.g., from Boehringer Mannheim Corp., Indianapolis, Ind.; New England Biolabs, Inc., Beverley, Mass.; Pharmacia LKB Biotechnology, Inc., Piscataway, N.J.; Integrated DNA Technology, Coralville, Iowa; Eurogentec, San Diego, Calif.; Sigma Genesys, The Woodlands, TX). It is to be understood that a vast array of primers can be useful in the present invention, including those not specifically disclosed herein, without departing from the scope or preferred embodiments thereof. In some other embodiments, the nucleic acid primer is complementary to a portion of the RNA template.

F. Nucleotide Bases

Nucleotide bases useful in the present invention can be any nucleotide useful in the polymerization of a nucleic acid. Nucleotides can be naturally occurring, unusual, modified, derivative, or artificial. Nucleotides can be unlabeled, or detectably labeled by methods known in the art (e.g., using radioisotopes, vitamins, fluorescent or chemiluminescent moieties, dioxigenin). Preferably the nucleotides are deoxynucleoside triphosphates, dNTPs (e.g., dATP, dCTP, dGTP, dTTP, dITP, dUTP, α-thio-dNITs, biotin-dUTP, fluorescein-dUTP, digoxigenin-dUTP, 7-deaza-dGTP). dNTPs are also well known in the art and are commercially available venders (e.g., from Boehringer Mannheim Corp., Indianapolis, Ind.; New England Biolabs, Inc., Beverley, Mass.; Pharmacia LKB Biotechnology, Inc., Piscataway, N.J.).

The nucleotides of the present invention can be present in any concentration. In some embodiments, the nucleotides is present in an amount from about 1 µM to about 1000 µM. In other embodiments, the nucleotides is present in an amount from about 10 µM to about 750 µM. In still other embodiments, the nucleotides is present in an amount from about 100 µM to about 500 µM. One of skill in the art will appreciate that other concentrations of nucleotides are useful in the present invention.

G. Buffering Agents and Salts

Buffering agents and salts useful in the present invention provide appropriate stable pH and ionic conditions for nucleic acid synthesis, e.g., for reverse transcriptase and DNA polymerase activity. A wide variety of buffers and salt solutions and modified buffers are known in the art that can be useful in the present invention, including agents not specifically disclosed herein. Preferred buffering agents include, but are not limited to, TRIS, TRICINE, BIS-TRICINE, HEPES, MOPS, TES, TAPS, PIPES, CAPS. Preferred salt solutions include, but are not limited to solutions of, potassium acetate, potassium sulfate, potassium chloride, ammonium sulfate, ammonium chloride, ammonium acetate, magnesium chloride, magnesium acetate, magnesium sulfate, manganese chloride, manganese acetate, manganese sulfate, sodium chloride, sodium acetate, lithium chloride, and lithium acetate.

The buffering agents of the present invention can be present in any concentration. In some embodiments, the buffer is present in an amount from about 0.1 mM to about 1000 mM. In other embodiments, the buffer is present in an amount from about 1 mM to about 500 mM. In still other embodiments, the buffer is present in an amount from about 5 mM to about 250 mM. One of skill in the art will appreciate that other concentrations of buffer are useful in the present invention.

The salts of the present invention can be present in any concentration. In some embodiments, the salt is present in an amount from about 0.01 mM to about 1000 mM. In other embodiments, the salt is present in an amount from about 0.1 mM to about 500 mM. In still other embodiments, the salt is present in an amount from about 1 mM to about 100 mM. One of skill in the art will appreciate that other concentrations of salts are useful in the present invention.

H. Other Additives

Other additives capable of facilitating reverse transcription, replication, and/or a combination of both reactions (e.g., agents for facilitating RT-PCR), other than those disclosed for the first time by this invention, are known in the art. In accordance with the compositions and methods of this invention, one or more of these additives can be incorporated in the present compositions to optimize the generation and replication of nucleic acids from a ribonucleic acid template. Additives can be organic or inorganic compounds. Inhibition-relieving agents useful in the present invention include, but are not limited to, polypeptides such as; human serum albumin, bovine serum albumin (BSA), ovalbumin, albumax, casein, gelatin, collagen, globulin, lysozyme, transferrin, myoglobin, hemoglobin, α-lactalbumin, fumarase, glyceraldehyde-3-phosphate dehydrogenase (GAPDH), amyloglucosidase, carbonic anhydrase, β-lactoglobulin, aprotinin, soybean trypsin inhibitor, trypsinogen, phosphorylase b, myosin, actin, β-galactosidase, catalase, tryptic soy digests, tryptose, lectins, *E. coli* single-stranded binding (SSB) protein, phage T4 gene 32 protein, and the like, or fragments or derivatives thereof. Examples of nonpolypeptide additives include, but are not limited to; tRNA, rRNA, sulfur-containing compounds, acetate-containing compounds, dimethylsulfoxide (DMSO), glycerol, formamide, betain, tetramethylammonium chloride (TMAC), polyethylene glycol (PEG), TWEEN 20 non-ionic surfactant, NP 40, non-ionic surfactant, ectoine, and polyols. Preferred additives include DMSO, glycerol, formamide, betain, TMAC, PEG, TWEEN 20 non-ionic surfactant, NP 40 non-ionic surfactant, ectoine, polyols, E. coli (SSB) protein, Phage T4 gene 32 protein, BSA.

In addition, amplification can be performed in the presence of agents which provide a means for detection of the amplification products. For example, the reaction vessel can already contain appropriate hybridization probes for homogenous real time detection of amplification products. Preferably, these probes can be appropriately labeled with fluorescent moieties. Other components include dyes that bind to double-stranded DNA. In some embodiments, the dye can be SYBR green. One of skill in the art will appreciate that other dyes are useful in the present invention.

II. Compositions and Kits

In some embodiments, the present invention also provides compositions having a reverse transcriptase, a DNA polymerase, and a RT inhibition reducer that can be Sso7d, Sac7d, Sac7e, Sso7e, AluI methylase, suramin, a phosphorothioate oligodeoxycytosine, a phosphorothioate oligodeoxyadenine, a phosphorothioate oligodeoxythymine and poly(rA)(dT). In some other embodiments, the RT inhibition reducer is phosphorothioate oligodeoxycytosine (SdC). In still other embodiments, the composition can also include at least one of buffers, nucleotides, salts, stabilizers, primers or nuclease-free water.

In another embodiment, the present invention provides a kit having a first solution mixture including a DNA polymerase and a RT inhibition reducer that can be Sso7d, Sac7d, Sac7e, Sso7e, AluI methylase, suramin, a phosphorothioate oligodeoxycytosine, a phosphorothioate oligodeoxyadenine, a phosphorothioate oligodeoxythymine or poly(rA)(dT). The kit optionally includes at least one of buffers, nucleotides, salts, stabilizers, instructions, primers, RNA templates, dyes and nuclease-free water. Both solution mixtures together with primers and RNA template will enable RT-PCR of the selected RNA target. Any of the optional buffers, nucleotides, salts, stabilizers, instructions, primers, RNA templates and nuclease-free water can be individually present in either the first solution, or present in one or more separate solutions.

In other embodiments, the kit also includes a reverse transcriptase. In some other embodiments, the reverse transcriptase is in the first solution. In still other embodiments, the kit includes a second solution having the reverse transcriptase. In yet other embodiments, the first solution further comprises a buffer, nucleotides and salts, and a third solution comprises nuclease-free water. In still yet other embodiments, the first solution further comprises a buffer, nucleotides, a dye and salts, and a third solution comprises nuclease-free water.

In some embodiments, the RT inhibition reducer is a member selected from the group consisting of Sso7d, AluI methylase, suramin, phosphorothioate oligodeoxycytosine and poly(rA)(dT). In other embodiments, the RT inhibition reducer is a phosphorothioate oligodeoxycytosine (SdC). In some other embodiments, the DNA polymerase is Taq. In still other embodiments, the reverse transcriptase is M-MLV reverse transcriptase. In yet other embodiments, the salts can each be a magnesium salt, an ammonium salt, a potassium or a combination thereof. In still yet other embodiments, the kit can further comprise nuclease-free water.

Stabilizers useful in the present invention include, but are not limited to, polyol (glycerol, threitol, etc.), a polyether including cyclic polyethers, polyethylene glycol, organic or inorganic salts, such as ammonium sulfate, sodium sulfate, sodium molybdate, sodium tungstate, organic sulfonate, etc., sugars, polyalcohols, amino acids, peptides or carboxylic acids, a quencher and/or scavenger such, as mannitol, glycerol, reduced glutathione, superoxide dismutase, bovine serum albumin (BSA) or gelatine, spermidine, dithiothreitol (or mercaptoethanol) and/or detergents such as TRITON® X-100 [Octophenol(ethyleneglycolether)], THESIT® [Polyoxyethylene 9 lauryl ether (Polidocanol $C_{12}E_9$)], TWEEN® (Polyoxyethylenesorbitan monolaurate 20, NP40) and BRIJ®-35 (Polyoxyethylene23 lauryl ether). One of skill in the art will appreciate that other stabilizers are useful in the present invention.

Compositions and kits of the present invention can also include hybridization probes. A hybridization probe is a fragment of DNA that is used to detect the presence of nucleotide sequences in DNA or RNA samples. The probe hybridizes to a complementary portion of single-stranded nucleic acid (DNA or RNA). The hybridization probes can be any length, usually 100-1000 bases long. The hybridization probes useful in the present invention can be labeled, radioactively or via a fluorophore, for example, in order to facilitate detection.

III. Examples

Example 1

Reduction of RT Inhibition in RT-PCR

Thaw all components, except the reverse transcriptase, at room temperature. Mix gently, but thoroughly, and then centrifuge at 4° C. to collect contents to the bottom of the tube. Chill on ice before using. Centrifuge again briefly at 4° C. if needed.

To a mixture of Taq DNA polymerase, dNTP (dATP, dCTP, dGTP and dTTP), magnesium chloride, stabilizers and SdC, is added a forward primer, a reverse primer, nuclease-free water and a reverse transcriptase. Assemble the reaction cocktail with all required components except sample template (total RNA) and dispense equal aliquots into each reaction tube. Add target sample (RNA template) to each reaction as the final step 5-10 µl volumes.

The reaction mixture is then incubated in a real-time thermal detection system as follows:

cDNA synthesis: 10 min at 50° C.

reverse transcriptase inactivation: 5 min at 95° C.

PCR cycling and detection (30 to 45 cycles): 10 sec at 95° C., followed by 30 sec at 55° C. to 60° C.

Example 2

Kit

Kits can be prepared according to the following concentrations:

| Component | Kit 1 First Reaction Mixture (Conc.) | Kit 1 Second Reaction Mixture (Conc.) | Kit 2 First Reaction Mixture (Conc.) | Kit 2 Second Reaction Mixture (Conc.) | Kit 3 (Conc.) | Kit 4 (Conc.) |
|---|---|---|---|---|---|---|
| Buffer | Hepes 10-100 mM | | Tris 20-140 mM | | Tris 20-140 mM | Hepes 10-100 mM |
| DNA Polymerase | iTaq 25-50 Units/mL | | iTaq 25-50 Units/mL | | iTaq 25-50 Units/mL | iTaq 25-50 Units/mL |
| dNTP | 200-400 µM | | 200-400 µM | | 200-400 µM | 200-400 µM |
| Salt | $Mg^{2+}$ 1-10 mM $(NH_4)SO_4$ 2-15 mM | | $Mg^{2+}$ 1-10 mM KCl 10-140 mM | | $Mg^{2+}$ 1-10 mM KCl 10-140 mM | $Mg^{2+}$ 1-10 mM $(NH_4)SO_4$ 2-15 mM |
| SdC | 6 nM | | 5 nM | | 5 nM | 6 nM |
| Other | SYBR Green 0.1x-0.6x | | | | | SYBR Green 0.1x-0.6x |
| Reverse Transcriptase | | M-MLV 10-40 Units/µL | | M-MLV 10-40 Units/µL | M-MLV 10-40 Units/µL | M-MLV 10-40 Units/µL |

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A composition comprising:
   a reverse transcriptase;
   a DNA primer; and
   a reverse transcriptase inhibition reducer, wherein the reverse transcriptase inhibition reducer is a phosphorothioate oligodeoxynucleotide, wherein the phosphorothioate oligodeoxynucleotide is phosphorothioate oligodeoxycytosine (SdC), phosphorothioate oligodeoxyadenine (SdA), phosphorothioate oligodeoxythymine (SdT), or phosphorothioate oligodoxyguanosine (SdG), and wherein the phosphorothioate oligodeoxynucleotide is present in an amount from 0.01 nM to 25 nM.

2. The composition of claim 1, wherein the phosphorothioate oligodeoxynucleotide is SdC.

3. The composition of claim 1, wherein the phosphorothioate oligodeoxynucleotide is present in an amount from 0.1 nM to 10 nM.

4. The composition of claim 1, wherein the phosphorothioate oligodeoxynucleotide is at least an 18-mer.

5. The composition of claim 1, wherein the reverse transcriptase is Avian Myeloblastosis Virus reverse transcriptase (AMV-RT), Moloney Murine Leukemia Virus reverse transcriptase (M-MLV-RT), Human Immunovirus reverse transcriptase (HIV-RT), Equine Infectious Anemia Virus reverse transcriptase (EIAV-RT), Rous-associated Virus 2 (RAV2-RT), recombinant Thermus thermophilus (rTth) DNA polymerase, or Z05 DNA polymerase.

6. The composition of claim 5, wherein the reverse transcriptase is M-MLV-RT.

7. The composition of claim 1, wherein the DNA primer is an oligo dT, a random hexamer, or a gene-specific primer.

8. The composition of claim 1, further comprising at least one member selected from the group consisting of buffers, nucleotides, salts, stabilizers, and nuclease-free water.

9. The composition of claim 8, wherein the salts are selected from the group consisting of a magnesium salt, an ammonium salt, a potassium salt, and a combination thereof.

10. The composition of claim 1, further comprising a DNA polymerase.

11. The composition of claim 10, wherein the DNA polymerase is a thermostable polymerase.

12. The composition of claim 10, wherein the DNA polymerase is Taq DNA polymerase.

* * * * *